(12) United States Patent
Tsals

(10) Patent No.: US 9,089,655 B2
(45) Date of Patent: Jul. 28, 2015

(54) INTRADERMAL INJECTION ADAPTER

(75) Inventor: Izrail Tsals, Newtown, PA (US)

(73) Assignee: SID Technologies, LLC, Newtown, PA (US)

( * ) Notice: Subject to any disclaimer, the term of this patent is extended or adjusted under 35 U.S.C. 154(b) by 352 days.

(21) Appl. No.: 13/386,099

(22) PCT Filed: Jul. 23, 2010

(86) PCT No.: PCT/US2010/043071
§ 371 (c)(1),
(2), (4) Date: Jan. 20, 2012

(87) PCT Pub. No.: WO2011/011697
PCT Pub. Date: Jan. 27, 2011

(65) Prior Publication Data
US 2012/0123386 A1 May 17, 2012

Related U.S. Application Data

(60) Provisional application No. 61/271,565, filed on Jul. 23, 2009, provisional application No. 61/283,249, filed on Dec. 2, 2009, provisional application No. 61/343,045, filed on Apr. 23, 2010.

(51) Int. Cl.
*A61M 5/00* (2006.01)
*A61M 5/46* (2006.01)
*A61M 5/32* (2006.01)

(52) U.S. Cl.
CPC ............. *A61M 5/46* (2013.01); *A61M 5/3287* (2013.01)

(58) Field of Classification Search
CPC ... A61M 5/158; A61M 5/178; A61M 5/3134; A61M 5/31565; A61M 5/3202; A61M 5/3204; A61M 5/321; A61M 5/3213; A61M 5/3216; A61M 5/3219; A61M 5/322; A61M 5/3243; A61M 2005/158; A61M 2005/178; A61M 2005/2006; A61M 2005/31565; A61M 2005/321; A61M 2005/3213; A61M 2005/3216; A61M 2005/3243; A61M 5/46; A61M 5/3287
USPC .................. 604/116, 117, 162, 187, 192, 506
See application file for complete search history.

(56) References Cited

U.S. PATENT DOCUMENTS 2,198,666 A * 4/1940 Gruskin ........................ 604/117
2,701,566 A   2/1955 Krug
(Continued)

FOREIGN PATENT DOCUMENTS

| CN | 1520320 A | 8/2004 |
| EP | 0216460 B1 | 9/1990 |

(Continued)

OTHER PUBLICATIONS

U.S. Appl. No. 13/870,330 by Evans, filed Apr. 25, 2013.
(Continued)

*Primary Examiner* — Bhisma Mehta
*Assistant Examiner* — Nicholas Meghri
(74) *Attorney, Agent, or Firm* — Panitch Schwarze Belisario & Nadel LLP

(57) ABSTRACT

An intradermal injection assembly for injecting a medicament into skin could form an intradermal needle with an adapter, an intradermal syringe with an adapter or an adapter for a merger with a syringe with a cannula. The intradermal adapter in these devices has a body having a longitudinal axis, a central portion having a cannula channel and a distal protrusion extending generally parallel to the longitudinal axis. The distal protrusion of the adapter has a first skin contacting surface extending generally parallel to the longitudinal axis. At least a portion of the distal protrusion is generally transparent such that the portion of the cannula that extends distally relative to a demarcation plane can be viewed through the distal protrusion during insertion of the cannula into a patient's skin.

8 Claims, 13 Drawing Sheets

(56) References Cited

U.S. PATENT DOCUMENTS

| | | | |
|---|---|---|---|
| 3,324,854 | A | 6/1967 | Weese |
| 3,459,177 | A | 8/1969 | Deuschle |
| 3,472,227 | A | 10/1969 | Burke |
| 4,332,248 | A | 6/1982 | DeVitis |
| 4,393,870 | A | 7/1983 | Wagner |
| 4,631,057 | A | 12/1986 | Mitchell |
| 4,737,144 | A | 4/1988 | Choksi |
| 4,747,837 | A | 5/1988 | Hauck |
| 4,801,295 | A | 1/1989 | Spencer |
| 4,850,996 | A | 7/1989 | Cree |
| 4,958,625 | A | 9/1990 | Bates et al. |
| 4,998,920 | A | 3/1991 | Johnson |
| 5,053,018 | A | 10/1991 | Talonn et al. |
| 5,084,030 | A | 1/1992 | Byrne et al. |
| 5,108,378 | A | 4/1992 | Firth et al. |
| 5,197,953 | A | 3/1993 | Colonna |
| 5,282,793 | A | 2/1994 | Larson |
| 5,364,362 | A * | 11/1994 | Schulz ............................ 604/115 |
| 5,437,640 | A | 8/1995 | Schwab |
| 5,496,288 | A | 3/1996 | Sweeney |
| 5,520,653 | A * | 5/1996 | Reilly et al. .................. 604/152 |
| 5,527,287 | A | 6/1996 | Miskinyar |
| 5,669,888 | A | 9/1997 | Trapp |
| 5,855,839 | A | 1/1999 | Brunel |
| 5,893,845 | A | 4/1999 | Newby et al. |
| 6,117,108 | A | 9/2000 | Woehr et al. |
| 6,200,291 | B1 | 3/2001 | Di Pietro |
| 6,494,865 | B1 | 12/2002 | Alchas |
| 6,569,123 | B2 | 5/2003 | Alchas et al. |
| 6,607,509 | B2 * | 8/2003 | Bobroff et al. ................ 604/136 |
| 6,666,844 | B1 | 12/2003 | Igo et al. |
| 6,689,118 | B2 | 2/2004 | Alchas et al. |
| 6,776,776 | B2 | 8/2004 | Alchas et al. |
| 6,921,384 | B2 | 7/2005 | Reilly et al. |
| 6,939,322 | B2 * | 9/2005 | Crank et al. .................. 604/117 |
| 7,052,483 | B2 | 5/2006 | Wojcik |
| 7,938,808 | B2 | 5/2011 | Pessin |
| 8,083,715 | B2 | 12/2011 | Sonoda et al. |
| 8,556,861 | B2 | 10/2013 | Tsals |
| 2001/0056265 | A1 | 12/2001 | Heinz et al. |
| 2002/0077599 | A1 | 6/2002 | Wojcik |
| 2002/0193744 | A1 | 12/2002 | Alesi et al. |
| 2003/0050602 | A1 | 3/2003 | Pettis et al. |
| 2003/0093032 | A1 | 5/2003 | Py et al. |
| 2003/0199822 | A1 | 10/2003 | Alchas et al. |
| 2004/0010234 | A1 | 1/2004 | Hung et al. |
| 2004/0147901 | A1 | 7/2004 | Py et al. |
| 2006/0079920 | A1 | 4/2006 | Schraga |
| 2007/0118077 | A1 | 5/2007 | Clarke et al. |
| 2007/0250016 | A1* | 10/2007 | Pech et al. .................... 604/198 |
| 2008/0154205 | A1* | 6/2008 | Wojcik ..................... 604/164.01 |
| 2010/0137831 | A1 | 6/2010 | Tsals |
| 2011/0224609 | A1 | 9/2011 | Tsals et al. |

FOREIGN PATENT DOCUMENTS

| | | |
|---|---|---|
| EP | 0457477 A1 | 11/1991 |
| EP | 0702973 A2 | 3/1996 |
| EP | 2139543 A1 | 1/2010 |
| FR | 2612401 A1 | 9/1988 |
| FR | 2616331 A1 | 12/1988 |
| JP | 02-046861 A | 2/1990 |
| JP | 08-107933 A | 4/1996 |
| JP | H11-512016 A | 10/1999 |
| JP | 2005-021247 A | 1/2005 |
| JP | 2010524646 T | 7/2010 |
| WO | 9507722 A1 | 3/1995 |
| WO | 9526764 A1 | 10/1995 |
| WO | 9709077 A1 | 3/1997 |
| WO | 9741907 A2 | 11/1997 |
| WO | 02083216 A1 | 10/2002 |
| WO | 2006052737 A1 | 5/2006 |
| WO | 2008131440 A1 | 10/2008 |
| WO | 2010064211 A2 | 6/2010 |
| WO | 2010077596 A1 | 7/2010 |
| WO | 2011011697 A1 | 1/2011 |
| WO | 2011112916 A1 | 9/2011 |

OTHER PUBLICATIONS

Office Action issued May 15, 2012 in JP Application No. 2010-506461 (with English translation of relevant portions).
Office Action issued Mar. 2, 2012 in U.S. Appl. No. 12/597,103.
Office Action issued Aug. 2, 2013 in U.S. Appl. No. 13/057,006 by TSALS.
International Search Report Issued Aug. 4, 2011 in Int'l Application No. PCT/US2011/028072.
Office Action issued Aug. 10, 2012 in U.S. Appl. No. 12/597,103.
U.S. Appl. No. 13/583,096 by Tsals, filed Sep. 6, 2012.
Int'l Preliminary Report on Patentability issued Sep. 27, 2012 in Int'l Application No. PCT/US2011/028072.
Office Action issued Jun. 13, 2013 in CN Application No. 201080041235.5.
Office Action issued Nov. 22, 2013 in U.S. Appl. No. 13/583,096 by Tsals.
Office Action issued Jan. 14, 2014 in U.S. Appl. No. 13/355,031 by Tsals.
Int'l Preliminary Report on Patentability issued Apr. 9, 2012 in Int'l Application No. PCT/US10/43071.
Office Action issued Apr. 30, 2013 in JP Application No. 2012-521832.
Office Action issued Mar. 14, 2013 in U.S. Appl. No. 12/597,103.
Office Action issued Apr. 15, 2013 in U.S. Appl. No. 13/057,006.
Office Action issued Apr. 24, 2013 in U.S. Appl. No. 13/583,096.
International Search Report Issued Mar. 29, 2010 in Int'l Application No. PCT/US2009/066960.
Int'l Search Report issued Oct. 27, 2010 in Int'l Application No. PCT/US2010/043071; Written Opinion.
Int'l Search Report issued on Sep. 16, 2008 in Int'l Application No. PCT/US08/61331; Written Opinion.
Int'l Preliminary Report on Patentability Issued Aug. 14, 2009 in Int'l Application No. PCT/US08/61331.
Int'l Search Report issued on Mar. 23, 2006 in Int'l Application No. PCT/US05/39979.
Int'l Preliminary Report on Patentability Issued May 8, 2007 in Int'l Application No. PCT/US05/039979; Written Opinion.
U.S. Appl. No. 60/928,423, filed May 10, 2007.
Int'l Application No. PCT/US11/28072 filed Mar. 11, 2011.
Int'l Preliminary Report on Patentability issued Jun. 14, 2011 in Int'l Application No. PCT/US2009/066960.
Office Action issued Nov. 26, 2013 in JP Application No. 2012-521832.
Office Action issued Jan. 6, 2014 in U.S. Appl. No. 13/057,006 by Tsals.
Office Action issued Dec. 17, 2013 in EP Application No. 11 710 607.0.
Office Action issued Jul. 7, 2014 in CN Application No. 200980148920.5.
Int'l Search Report and Written Opinion issued May 27, 2014 in Int'l Application No. PCT/US2014/019907.
Office Action issued Apr. 8, 2014 in CN Application No. 201180013752.6.
English translation of an Office Action issued Apr. 11, 2014 in CN Application No. 201080041235.5.
Office Action issued May 5, 2014 in CN Application No. 200980148920.5.
English translation of an Office Action issued Sep. 29, 2014 in CN Application No. 201080041235.5.
Office Action issued Dec. 31, 2014 in U.S. Appl. No. 13/583,096 by Tsals.
Office Action issued Apr. 16, 2015 in U.S. Appl. No. 13/870,330 by Evans.
Office Action issued Apr. 28, 2015 in U.S. Appl. No. 13/583,096 by Tsals.

* cited by examiner

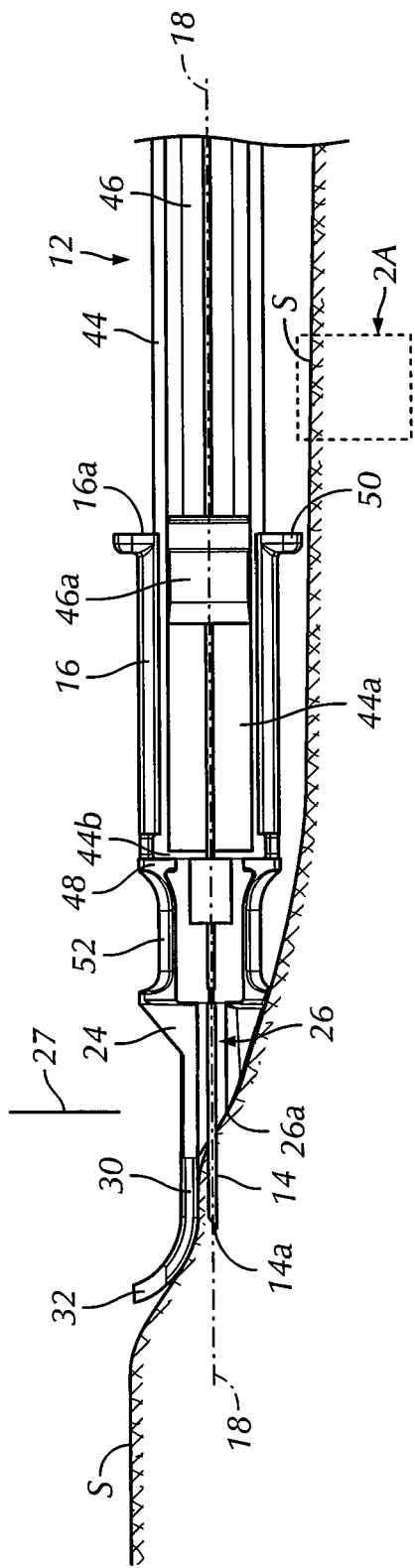
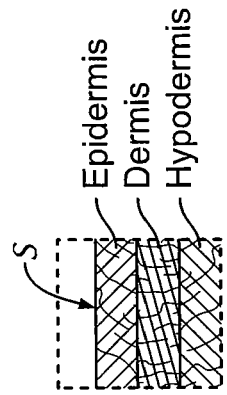
FIG. 2
FIG. 2A

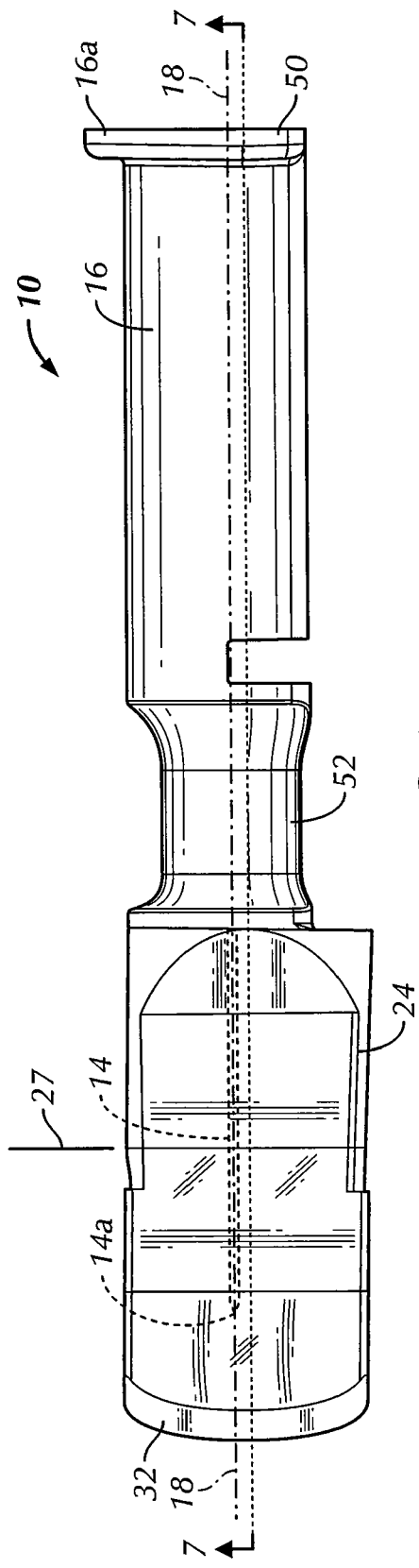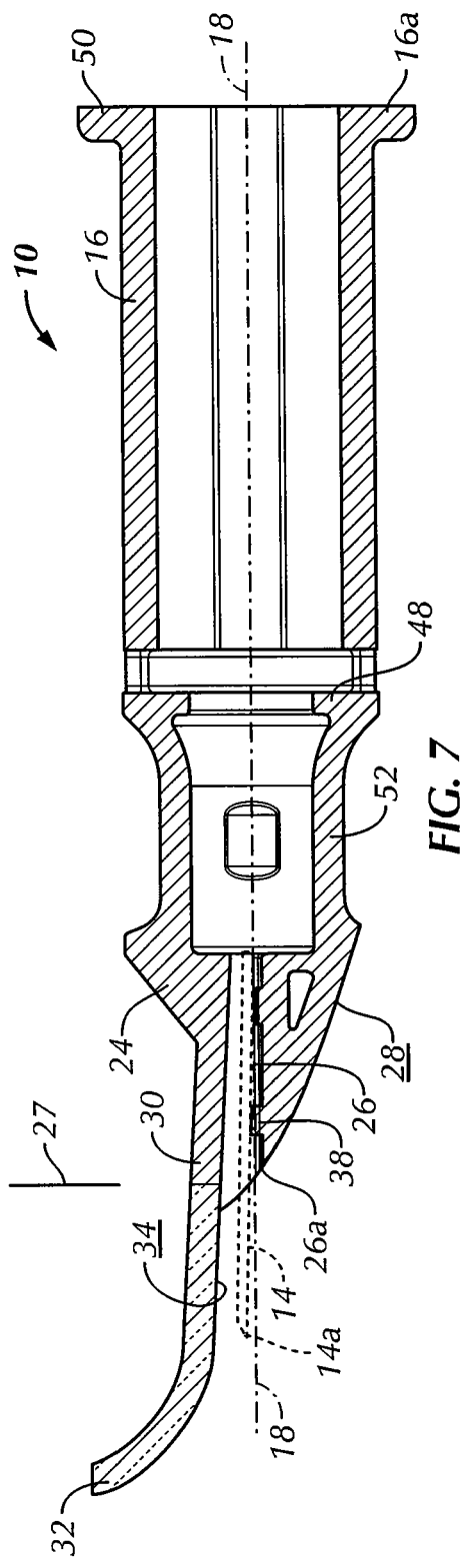
FIG. 6
FIG. 7

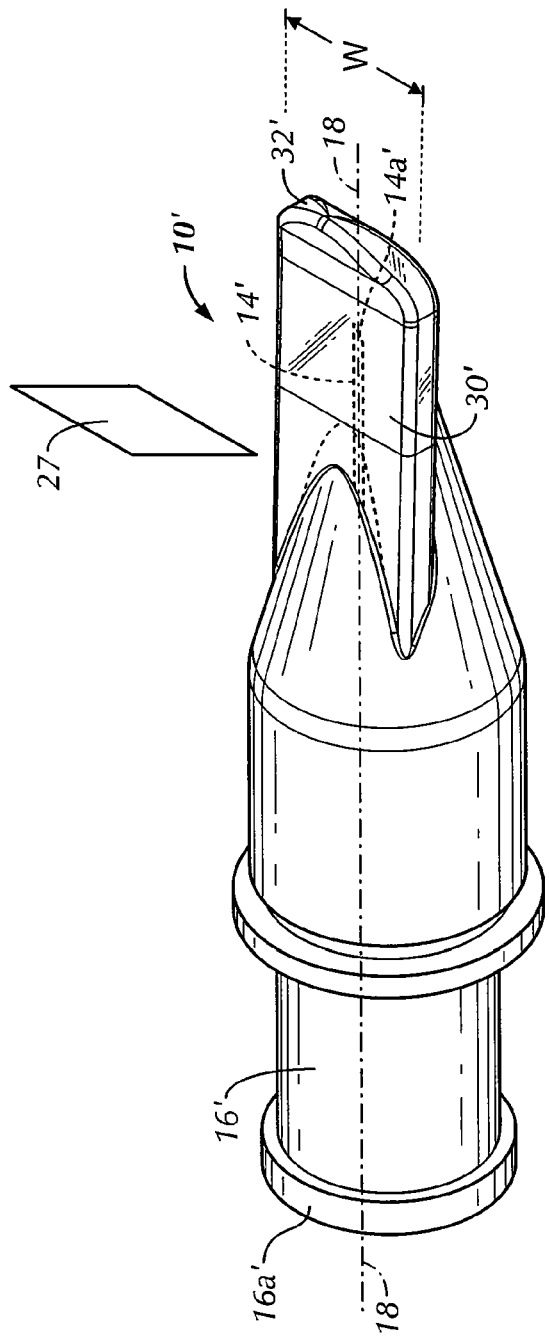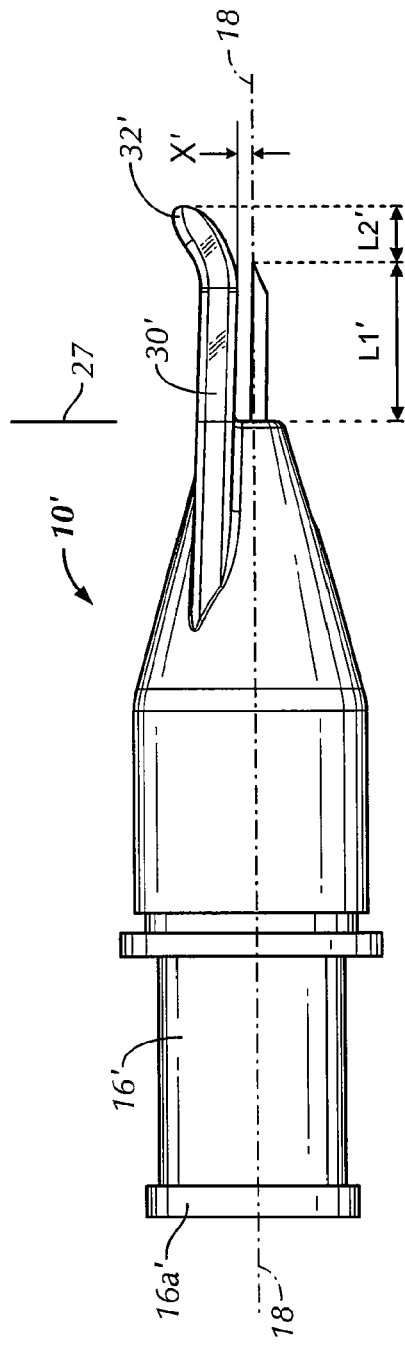
FIG. 11
FIG. 12

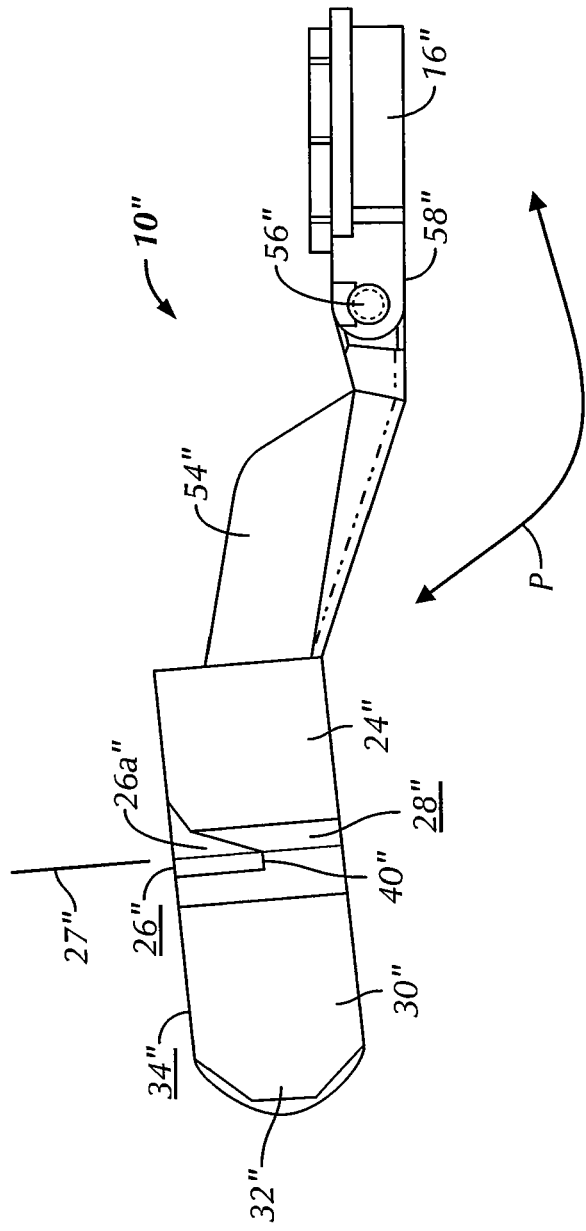
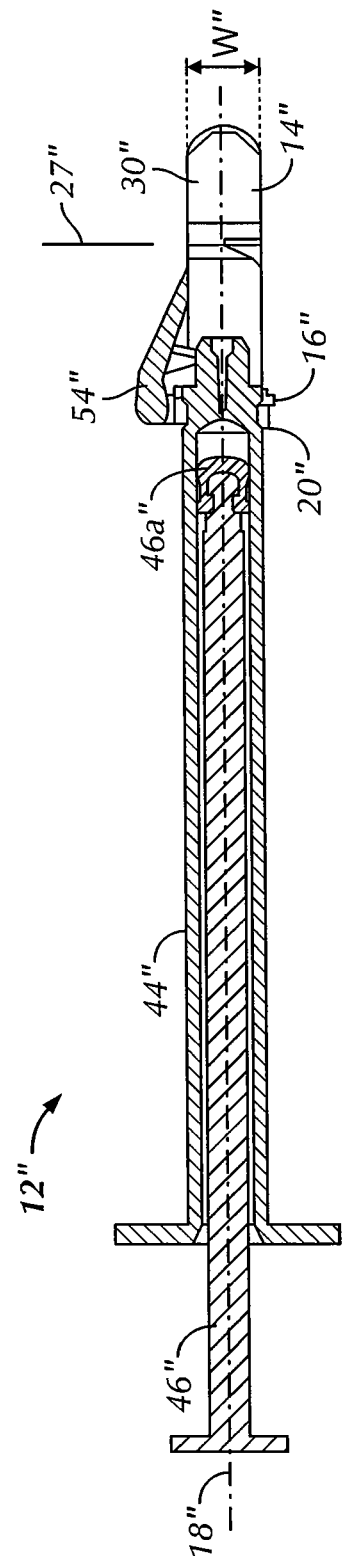
FIG. 13
FIG. 14

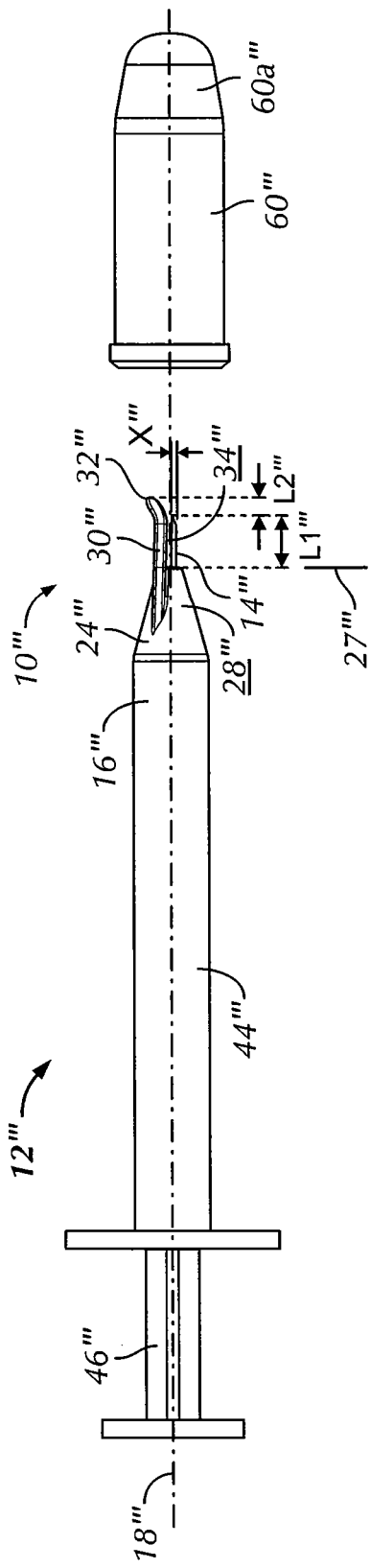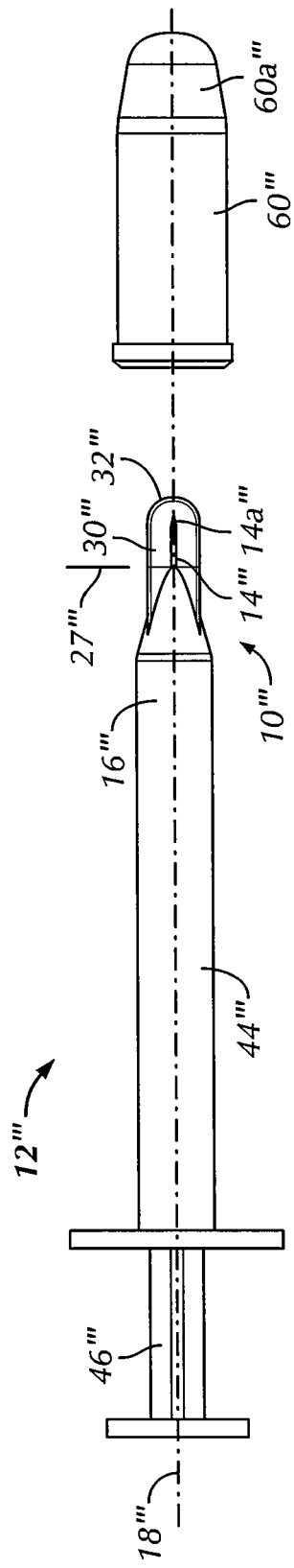

INTRADERMAL INJECTION ADAPTER

CROSS-REFERENCE TO RELATED APPLICATION

This application is a section 371 of International Application No. PCT/US2010/043071, filed Jul. 23, 2010, which was published in the English language on Jan. 27, 2011 under International Publication No. WO 2011/011697 which claims the benefit of U.S. Provisional Patent Application No. 61/271,565, filed Jul. 23, 2009, U.S. Provisional Patent Application No. 61/283,249, filed Dec. 2, 2009 and U.S. Provisional Patent Application No. 61/343,045, filed Apr. 23, 2010, the disclosures of which are incorporated herein by reference.

BACKGROUND OF THE INVENTION

Intradermal injections are used for delivering a variety of diagnostic and treatment compositions into a patient. Intradermal injections are typically injections of a relatively small amount of medicament into the dermis or dermal layer or even into a lower portion of the epidermis (FIG. 2A) of a patient's skin. Substances may be injected intradermally for diagnostic testing, such as to determine a patient's immunity status against tuberculosis and the status of allergic diseases. Vaccines, drugs and other compounds may also be delivered intradermally. In many instances, intradermal delivery is preferred because it generally requires a smaller volume dose of the diagnostic or treatment compound than other delivery techniques. There is considerable variation in the thickness of a patient's skin, both between individuals and within the same individual at different sites of the body. Generally the outer skin layer, or the epidermis, typically has a thickness between two hundred and five hundred microns (200-500 μm) and the dermis, the inner and thicker layer of the skin, generally has a thickness between one and one-half to three and one-half millimeters (1.5-3.5 mm).

Making intradermal injections is difficult and generally requires an experienced nurse or medical professional. Incorrect placement of the tip of the cannula may lead to a failed injection. The placement of the cannula tip deeper than about three millimeters (3.0 mm) has the potential of delivering the injection into the subcutaneous region, where the intradermal dosage may be insufficient. Incorrect placement of the cannula may also puncture the skin again after being inserted into dermis, with the delivered compound being lost on the surface of the skin. Injection is often followed by a jet effect, with the compound exiting the injection site through the puncture track. The jet effect is even more pronounced for injections through a cannula placed perpendicular to the injection site and in particular for shallow delivery. The success of intradermal injections is often determined by the skill and experience of the individual healthcare professional administering the injection. The preferred intradermal injection technique (using a standard cannula), requires the healthcare professional to stretch the skin, orient the cannula bevel to face upward, and insert a short bevel cannula at an angle of around ten to fifteen degrees)(10-15° relative to a surface of the skin, while also assuring that two to three millimeters (2-3 mm) of the cannula are located in the skin. The cannula tip ideally ends up positioned in the dermis or close to the dermis/epidermis boundary. The compound is slowly injected into the skin of the patient, forming a blister or wheal. The insertion of the cannula at an incorrect angle and/or depth results in a failed intradermal injection, which is typically repeated, causing additional pain and discomfort as well as ineffective treatment to the patient. Intradermal (ID) injection has been considered for immunization in the past, but has generally been rejected in favor of more reliable intramuscular or subcutaneous routes of administration because of the difficulty in making a successful ID injections, particularly when the injections are administered by relatively unskilled healthcare professionals.

Administration into the region of the intradermal space has been routinely used in the Mantoux tuberculin test, in which a purified protein derivative is injected at a shallow angle to the skin surface using a twenty-seven (27) or thirty (30) gauge cannula and a standard syringe. The technique is known to be quite difficult to perform and generally requires specialized training. A degree of imprecision in the placement of the injection results in a significant number of false negative test results. As a result, the Mantoux approach has not led to the use of intradermal injection for systemic administration of substances, despite the advantage of requiring smaller doses of substances, because the absorption of the medicament into the dermal skin layer is typically superior to injection of the same substance using alternative techniques.

It would be desirable to design and manufacture an intradermal injection adapter that provides a relatively simple, reliable intradermal injection, is relatively easy to use, is relatively cost effective to the user and limits waste of medicament. The cannula of the intradermal injection adapter is preferably statically mounted to or fixed relative to a body of the adapter and/or a barrel of a syringe in an assembled configuration.

BRIEF SUMMARY OF THE INVENTION

Briefly stated, in a preferred aspect, the present application is directed to a syringe assembly for delivery of intradermal injections comprising a syringe barrel having a proximal end and a distal end. A cannula is connected to the distal end of the syringe barrel. A protrusion is connected to the distal end of the syringe barrel, having a first skin contacting surface spaced from and generally parallel to the cannula. At least a portion of the protrusion proximate a distal end of the cannula is generally transparent to allow the cannula to be visible upon insertion into a patient's skin.

Additionally, the syringe assembly may comprise an adapter having a body with a proximal end and a distal end. The proximal end of the body is connectable to the distal end of the syringe barrel. The cannula is connected to the distal end of the body. And the protrusion is connected to the distal end of the body.

Further, the syringe assembly may comprise an adapter having a body with a proximal end and a distal end, wherein the body is connectable to the distal end of the syringe barrel. The protrusion is rotatably connected to the body. The protrusion may include a cannula support element to align the cannula to be generally parallel with the first skin contacting surface.

Still further, the syringe assembly may comprise an adapter having a body with a proximal end and a distal end wherein the body is connectable to the distal end of the syringe barrel and the protrusion is connected to the distal end of the body. A second skin contacting surface is connected to the distal end of the body. The cannula extends distally between the protrusion and the second skin contacting surface. At least one support element is connected to the body to align the cannula to be generally parallel with the first skin contacting surface In another aspect, a preferred embodiment of the present invention is directed to an intradermal injection adapter having a cannula for making an intradermal injection. The adapter includes a body having a longitudinal axis, a central portion and a distal protrusion. The central portion is located distally relative to the body along the longitudinal axis. The central portion has a cannula channel therethrough extending generally parallel to the longitudinal axis. The cannula channel defines a cannula channel edge. The distal protrusion has a first skin contacting surface extending generally parallel to the longitudinal axis. The first skin contacting surface is spaced from the cannula such that a distal portion of the cannula extends generally parallel to the first skin contacting surface. The distal protrusion is generally transparent distally relative to a demarcation plane defined where the cannula extends across the cannula channel edge such that the distal portion of the cannula can be viewed through the distal protrusion during insertion of the cannula into a patient's skin.

In another aspect, a preferred embodiment of the present invention is directed to an intradermal injection assembly for injecting a medicament into a dermal skin layer. The assembly includes a syringe including a cannula, a hub, a barrel and a plunger and an adapter having a body with a syringe channel, a central portion and a distal protrusion. The barrel has a generally cylindrical configuration and a hollow internal cavity adapted to receive the medicament therein. The central portion has a cannula channel defining a cannula channel edge. The distal protrusion has a distal nose. The adapter also includes a proximal end portion and a longitudinal axis extending between the proximal end portion and the distal nose. The distal protrusion includes a first skin contacting surface positioned generally parallel to the longitudinal axis. A distal portion of the cannula is spaced from the first skin contacting surface at a cannula gap distance in the assembled configuration. A tip of the cannula is positioned distally relative to the cannula channel edge in an assembled configuration.

In yet another aspect, a preferred embodiment of the present invention is directed to a method of injecting a medicament into a dermal skin layer of a patient's skin utilizing an adapter and syringe assembly including a distal protrusion having a relatively transparent portion distally relative to a demarcation plane defined where a cannula crosses a cannula channel edge and a relatively opaque portion proximally relative to the demarcation plane. The adapter also includes a first skin contacting surface positioned generally parallel to a distal portion of the cannula, a central portion and a longitudinal axis. The method includes the steps of placing the adapter proximate the patient's skin such that the longitudinal axis is generally parallel to the users skin, applying a force to the assembly toward the skin and generally parallel to the skin to slide the adapter and syringe assembly along the patient's skin and insert the cannula into the patient's skin, visually monitoring the insertion of the cannula into the users skin and the positioning of the patient's skin relative to the first skin contacting surface through the relatively transparent portion of the distal protrusion, confirming that the cannula is at least partially positioned within the patient's skin in an injection position, and injecting the medicament into the dermal skin layer.

In a further aspect, the present application is directed to an intradermal injection adapter for mounting to a syringe having a cannula for making an intradermal injection. The adapter includes a body having a longitudinal axis and a syringe channel configured to receive at least a portion of the syringe therein. A central portion has a cannula channel extending generally parallel to the longitudinal axis. The cannula channel defines a cannula channel edge. A distal protrusion extends generally parallel to the longitudinal axis. The distal protrusion has a first skin contacting surface extending generally parallel to the longitudinal axis. The first skin contacting surface is spaced from the longitudinal axis and is generally continuous between an area adjacent a tip of the cannula and an area adjacent the cannula channel edge in an assembled configuration. The distal protrusion is generally transparent distally and generally opaque proximally relative to a demarcation plane defined where the cannula extends over the cannula channel edge. The demarcation plane is generally perpendicular the longitudinal axis. The tip is positioned distally relative to the demarcation plane in the assembled configuration

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 2 is a side elevational view of the syringe mounted to the adapter of FIG. 1 in an assembled configuration with the cannula inserted into a patient's skin in the process of making an intradermal injection;

FIG. 2A is a cross-sectional view of the patient's skin taken from within box 2A of FIG. 2;

FIG. 6 is a top plan view of the adapter of FIG. 1;

FIG. 7 is a cross-sectional view of the adapter of FIG. 1, taken along line 7-7 of FIG. 6;

FIG. 11 is a top perspective view of an adapter in accordance with a second preferred embodiment of the present application;

FIG. 12 is a right-side elevational view of the adapter of FIG. 11;

FIG. 13 is a bottom plan view of an adapter in accordance with a third preferred embodiment of the present application;

FIG. 14 is a bottom plan, cross-sectional view of the adapter of FIG. 13 mounted to a syringe in an injection position;

FIG. 16 is a right-side elevational, partially exploded view of an adapter and syringe in accordance with a fourth preferred embodiment of the present application; and FIG. 17 is a top plan, partially exploded view of the adapter and syringe of FIG. 16.

DETAILED DESCRIPTION OF THE INVENTION

Figure 1:
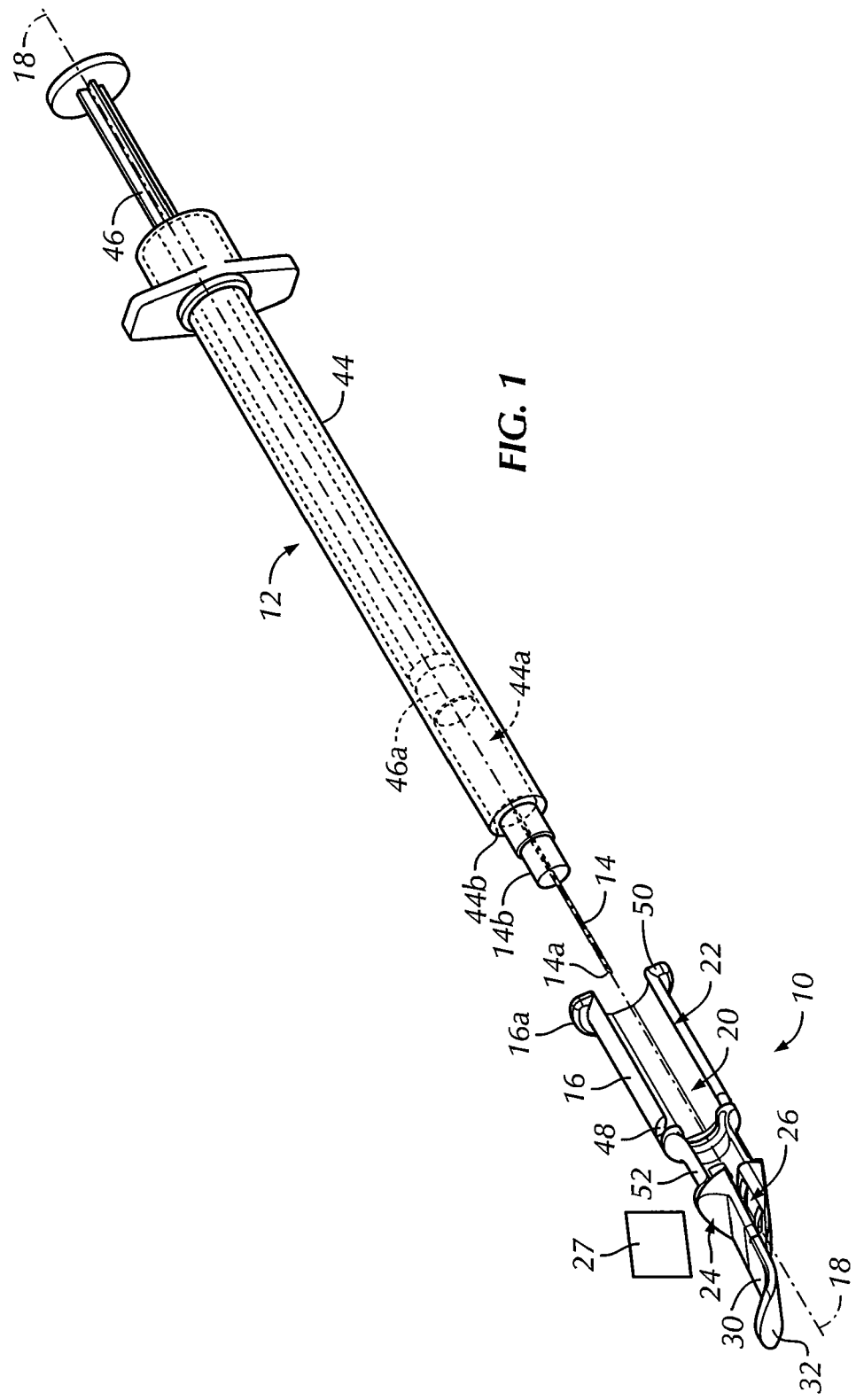
FIG. 1 is a top perspective view of a syringe and an adapter in accordance with a first preferred embodiment of the present invention.

Certain terminology is used in the following description for convenience only and is not limiting. The words "right," "left," "lower," and "upper" designate directions in the drawings to which reference is made. The words "inwardly" or "proximally" and "outwardly" or "distally" refer to directions toward and away from, respectively, the geometric center or orientation of the adapter, adapter and syringe assembly or other related parts thereof. The words, "connect", "connectable" and "connected" mean joined or linked together, either by direct engagement or through intermediate components. The terminology includes the above-listed words, derivatives thereof and words of similar import.

Referring to FIGS. 1-10, a first preferred embodiment of the present invention is directed to an intradermal injection adapter 10 for mounting to a syringe 12 having a cannula 14 for making an intradermal injection in a patient's skin S. In the first preferred embodiment, the adapter includes a side opening 22 that extends along an entire length of the adapter 10, generally parallel to the longitudinal axis 18. The side opening 22 permits insertion of the syringe 12 into the adapter 10 for injecting medicament into a patient in an assembled configuration, wherein a tip 14a of a cannula 14 is spaced distally relative to a cannula channel edge 26a of the adapter 10 and is generally fixed in this position in the assembled configuration. The side opening 22 specifically permits a medical professional to engage the syringe 12 with the adapter 10 prior to injection of the medicament into the patient. Typically, the adapter 10 is packaged in a sterile package and removed from the package for assembly with the syringe 12 prior to injecting the medicament into the patient. Accordingly, a plurality of packaged adapters 10 and a plurality of syringes 12 can be stored at an injection site and assembled when necessary for injecting medicament into patients.

The adapter 10 is not limited to inclusion of the side opening 22 (See FIGS. 11-17), but the side opening 22 permits relatively easy assembly or engagement of the syringe 12 with the adapter 10. For example, the adapter 22 may be sold as an individual, sterile unit to a medical organization or other user and mounted to a pre-filled syringe 12 before injection of the medicament into the skin S. However, the adapter 10 may also be configured to eliminate the side opening 22 such that the syringe 12 is introduced into the syringe channel 20 through a proximal end portion 16a of a body 16 of the adapter 10 (See FIGS. 13-15). In addition, the adapter 10 may be configured such that the adapter 10 is permanently affixed to or molded to the syringe 12 wherein the body 16 is permanently attached, adhesively bonded, formed or is otherwise permanently affixed or attached to the syringe 12 (See FIGS. 16 and 17). The adapter 10 is preferably used by healthcare professionals, but may also be used by non-healthcare professionals, potentially for self-injection and typically when the adapter 10 is pre-assembled to the syringe 12 (See e.g. FIGS. 16 and 17).

The intradermal injection adapter 10 also includes a central portion 24 having a cannula channel therethrough extending generally parallel to the longitudinal axis 18. The cannula channel defines the cannula channel edge 26a that tapers slightly distally in the first preferred embodiment, but may be oriented generally perpendicular or otherwise to the longitudinal axis 18. For example, the cannula channel edge 26a may be oriented in various configurations or at various orientations to accommodate introduction of the cannula 14 into the cannula channel 26, to align the cannula 14 with the adapter 10 or for various other design considerations. In the assembled configuration, at least a portion of the cannula 14 is received within the cannula channel 26 and a distal portion of the cannula 14 extends beyond the cannula channel 26. The cannula channel edge 26a is not limited to being positioned generally perpendicular to the longitudinal axis 18 and may be pitched or otherwise oriented relative to the longitudinal axis 18 and is slightly pitched relative to the longitudinal axis 18 in the first preferred embodiment (See FIGS. 4 and 9). In the first preferred embodiment, a demarcation plane 27 is defined where the cannula 14 extends over the channel edge 26a, is generally perpendicular to the longitudinal axis 18 and intersects the longitudinal axis 18. The tip 14a of the cannula 14 is positioned distally relative to the demarcation plane 27 when the syringe 12 and the adapter 10 are in the assembled configuration and the cannula 14 and tip 14a generally maintain their position relative to the demarcation plane 27 in the assembled configuration and through the injection process.

In the first prepared embodiment, a second skin contacting surface 28 extends proximally from the cannula channel edge 26a at a taper angle Δ. The taper angle Δ may be set or adapted to accommodate dimensions of the adapter 10 and/or the associated syringe 12. At least a portion of the second skin contacting surface 28 preferably tapers proximally from the channel edge 26a at a relatively shallow angle such that the second skin contacting surface 28 may smoothly slide along the patient's skin S. The second skin contacting surface 28 is not limited to being generally planar or conical, may be oriented at different angles, may have a portion that is generally perpendicular relative to the longitudinal axis 18 (See FIGS. 12 and 16), may be arcuate or slightly curved or even have a portion that is generally linear and additional portions that are arcuate and/or curved.

A distal protrusion 30 extends generally parallel to the longitudinal axis 18 from the central portion 24. In the first preferred embodiment, the distal protrusion 30 includes a sloped distal nose 32 that curves away from the longitudinal axis 18. The sloped or curved distal nose 32 assists the user or medical professional in arranging the adapter 10 relative to the patient's skin S and generally limits scrapping or rough engagement of the distal nose 32 with the patient's skin S to limit the patient's pain and discomfort. The sloped or curved distal nose 32 also promotes a relatively smooth sliding of the adapter 10 along the patient's skin S while inserting the cannula 14 into the patient's skin S and guiding the adapter 10 along a path generally parallel or slightly pitched relative to the patient's skin S such that the cannula 14 is inserted into the patient's skin S with the tip 14a positioned in the dermis or dermal layer. The distal protrusion 30 is not limited to inclusion of the distal nose 32 that generally slopes away from the longitudinal axis 18 and may include a blunt-edge at a distal end, may be tapered or may be otherwise configured to assist the user or medical professional in positioning the adapter 10 relative to the patient's skin S.

In the first preferred embodiment, the distal protrusion 30 is generally transparent distally relative to the demarcation plane 27 such that the cannula 14 can be viewed through the distal protrusion 30 during insertion of the cannula 14 into the skin S and generally during the entire intradermal injection process. Having a generally transparent distal protrusion 30 permits the medical professional, nurse or even the patient to view the cannula 14 through the distal protrusion 30 to ensure that the cannula 14 and, particularly, the tip 14a is inserted into the patient's skin S during injection. For example, a medial professional may position the cannula 14 relative to the user's skin and inadvertently fail to penetrate the skin S in sloped or rough areas. Such a mis-insertion may cause the user or medical professional to activate the syringe 12 to eject the medicament without the tip 14a positioned in the skin S, thereby losing or wasting the medicament. Ejecting the medicament with a mis-placed cannula 14 wherein the cannula 14 is not positioned in the dermal layer of the patient's skin S wastes the medicament, which can be relatively expensive and often requires a second injection, thereby typically causing additional pain and discomfort for the patient. Such a situation may also result in the patient not being vaccinated, potentially without the knowledge of the medical professional or other user. Accordingly, it is preferred that the distal protrusion 30 is relatively transparent such that the medical professional, nurse and/or patient can confirm that the cannula 14 is positioned beneath the surface of the patient's skin S prior to injection. However, the distal protrusion 30 is not limited to being generally transparent and may be opaque.

The distal protrusion 30 includes a first skin contacting surface 34 that extends generally parallel to the longitudinal axis 18. In the injecting position, the first skin contacting surface 34 contacts the surface of the patient's skin S to position the tip 14a of the cannula 14 at a predetermined depth into the skin S such that the tip 14a is positioned in the dermal layer of the skin S and the medicament is injected into the dermal layer for absorption. The first skin contacting surface 34 is preferably not discontinuous or does not include an opening or hole at or near the tip 14a to limit the potential that the skin S pushes into the opening or hole, thereby causing the tip 14a to be positioned too deep into the patient's skin S or even in a subcutaneous space. Accordingly, the generally continuous first skin contacting surface 34 generally controls a distance between the tip 14a of the cannula 14 and the first skin contacting surface 34 to increase the likelihood that the tip 14a is positioned in the dermal layer in an injection position (FIG. 2).

In the first preferred embodiment, a first alignment ramp 36 is positioned within the cannula channel 26 and is configured to orient the cannula 14 generally parallel to the first skin contacting surface 34 in an assembled configuration (FIG. 2). Orienting the cannula 14 generally parallel to the first skin contacting surface 34 is preferred to control the spacing of the cannula 14 relative to the first skin contacting surface 34 such that the tip 14a is positioned in the dermal layer of the patient's skin S in the injection position (FIG. 2).

The adapter 10 of the first preferred embodiment also includes a second alignment ramp 38 positioned within the cannula channel 26 that is configured to orient the cannula 14, in cooperation with the first alignment ramp 36, generally parallel with the first skin contacting surface 34 in the assembled configuration. The second alignment ramp 38 is preferably positioned distally in the cannula channel 26 relative to the first alignment ramp 36 and the cannula 14 is preferably in facing engagement with the first and second alignment ramps 36, 38 in the assembled configuration. The adapter 10 is not limited to inclusion of either the first alignment ramp 36 or the second alignment ramp 38 to align at least the distal section of the cannula 14 generally parallel to the first skin contacting surface 34 and may include numerous alternative alignment mechanisms or no specific alignment mechanism in the central portion 24 or within the cannula channel 26. For example, the cannula channel 26 may include a V-shaped groove that aligns the cannula 14 generally parallel to the first skin contacting surface 34, a clamping mechanism that aligns the cannula 14 with the first skin contacting surface 34 or numerous alternative alignment mechanisms to preferably arrange the cannula 14 generally parallel to the first skin contacting surface 34. In addition, the cannula 14 is not necessarily oriented generally parallel to the first skin contacting surface 34 and may be alternatively arranged such that the tip 14a of the cannula 14 is configured for positioning in the dermal layer of the skin S without being aligned generally parallel to the first skin contacting surface 34.

Figure 3:
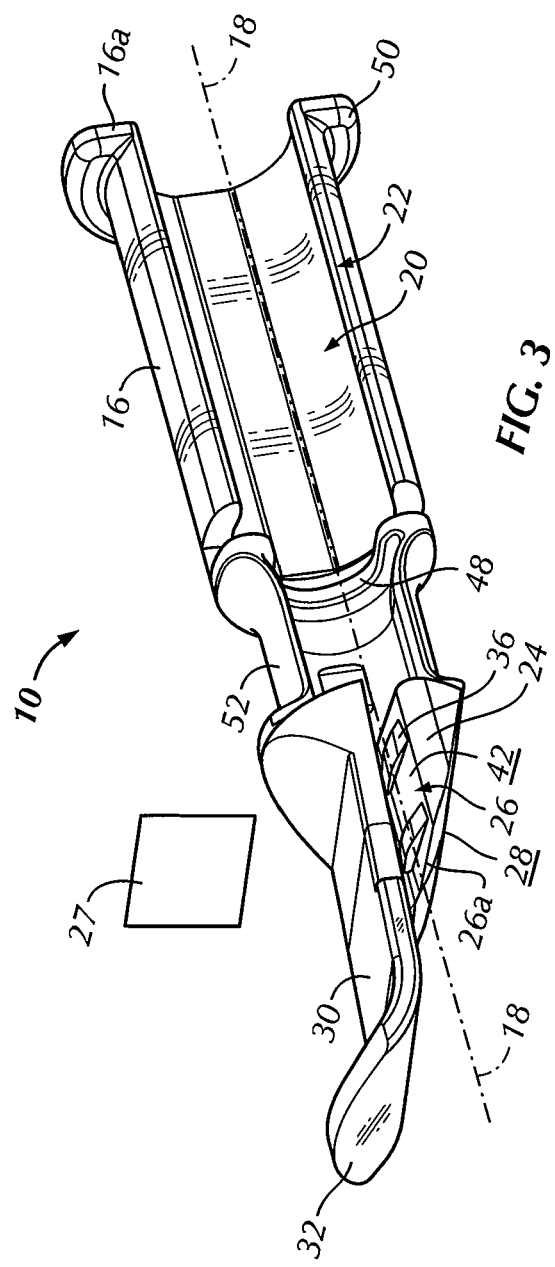
FIG. 3 is a front perspective view of the adapter of FIG. 1.
Figure 3A:
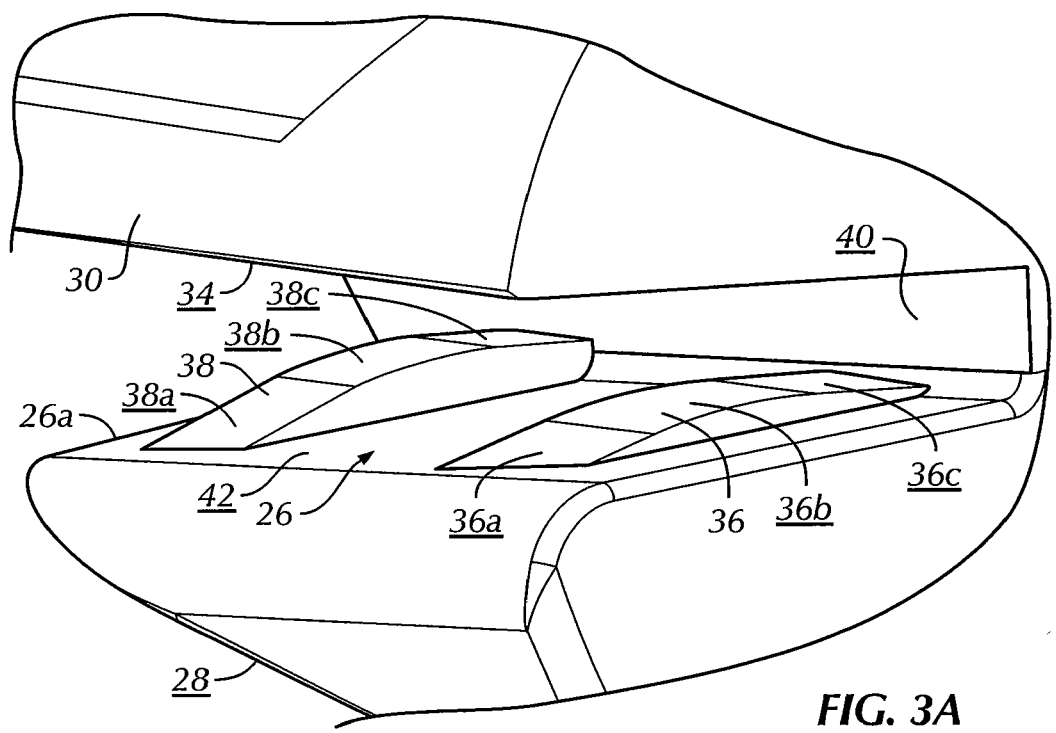
FIG. 3A is a magnified rear perspective view of a cannula channel of the adapter of FIG. 1.

Referring specifically to FIG. 3A, in the first preferred embodiment, the first and second alignment ramps 36, 38 include an upslope surface 36a, 38a, an apex surface 36b, 38b and a downslope surface 36c, 38c. The upslope surfaces 36a, 28a assist in guiding the cannula 14 through the side opening 22 into the cannula channel 26. The downslope surfaces 36c, 38c preferably urge the cannula 14 toward a lateral cannula wall 40 in the assembled configuration. The lateral cannula wall 40 preferably extends generally parallel to the longitudinal axis 18 at least adjacent the cannula channel 26. The cannula channel 26 is defined by the first skin contacting surface 34, the lateral cannula wall 40 and the alignment wall 42 in the first preferred embodiment and is generally contained in the central portion 24. The cannula 14 is preferably positioned adjacent the lateral cannula wall 40 in the assembled configuration. More specifically, the cannula 14 may be positioned in facing engagement with the downslope surfaces 36c, 38c of the first and second alignment ramps 36, 38 and with the lateral cannula wall 40 in the assembled configuration. Accordingly, the first and second alignment ramps 36, 38 and the lateral cannula wall 40 align the cannula 14 generally parallel to the first skin contacting surface 34 in the assembled configuration and generally center the cannula 14 along the longitudinal axis 18 in the assembled configuration. However, the cannula 14 is not limited to being aligned and centered utilizing the first and second alignment ramps 36, 38 and the lateral wall 40 as was described above and may be otherwise aligned and oriented by the adapter 10 such that the tip 14a is positioned in the dermal layer of the patient's skin in the injecting configuration. In addition, the cannula 14 is not limited to being generally coaxial with the longitudinal axis 18 in the assembled configuration and may be misaligned or slightly pitched relative to the longitudinal axis 18 as long as the tip 14 is generally positioned in the dermal layer in the injection position.

Figure 4:
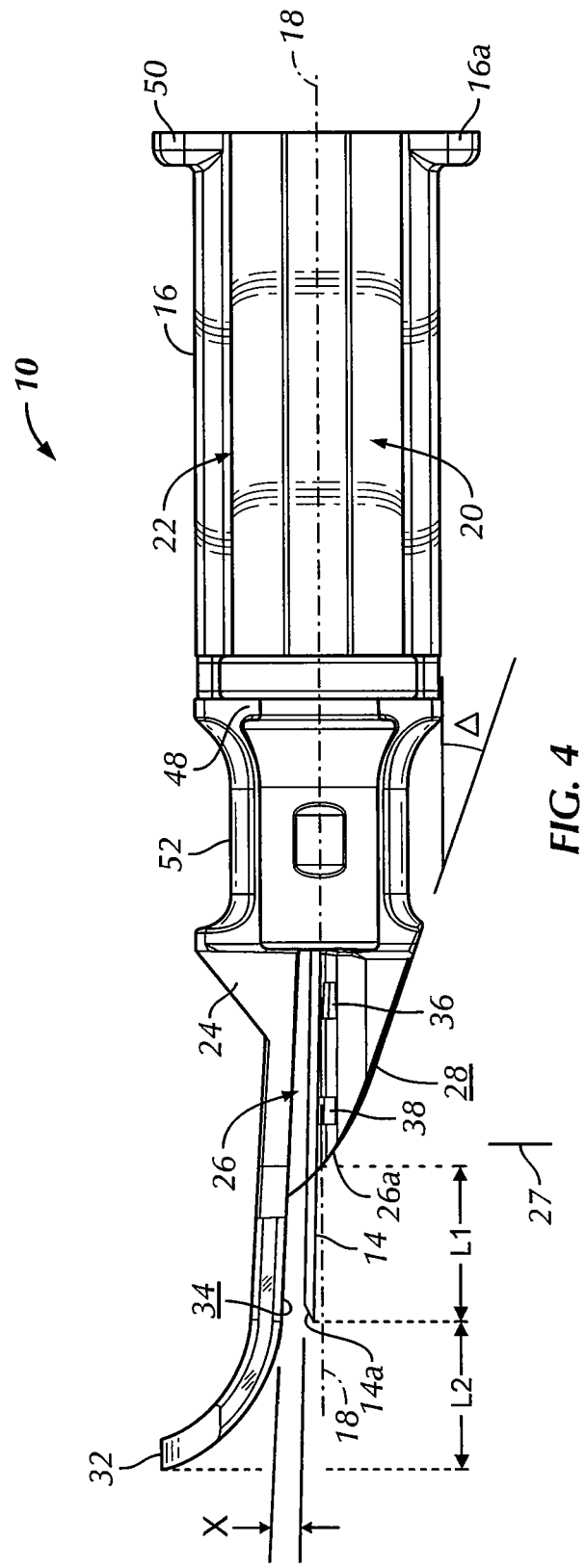
FIG. 4 is a side elevational view of the adapter of FIG. 1.

Referring to FIG. 4, the first skin contacting surface 34 is spaced a relatively consistent distance from the distal portion of the cannula 14. The first skin contacting surface 34 is also generally continuous between an area adjacent a tip 14a of the cannula 14 and an area adjacent the channel edge 26a in the assembled configuration. In the first preferred embodiment, the syringe 12 may be generally coaxial with the longitudinal axis 18 and the distal portion of the cannula 14 is pitched slightly upwardly away from the longitudinal axis 18 to come into generally parallel alignment with the first skin contacting surface 34 in the assembled configuration. The distal portion of the cannula 14 is preferably spaced at a cannula gap distance X from the first skin contacting surface 34. The cannula gap distance X is preferably at least two tenths of a millimeter (0.2 mm) and may be within a range of two tenths of a millimeter to two millimeters (0.2-2 mm). However, the cannula gap distance X is not limited to being in this range and may be comprised of nearly any distance that permits the tip 14a of the cannula 14 to be positioned in the dermal layer of the patient's skin S in the injection position. In the first preferred embodiment, the cannula gap distance X is approximately fifty-five hundredths of a millimeter (0.55 mm). In addition, a more preferred range for the cannula gap distance X is approximately four tenths of a millimeter to eight tenths of a millimeter (0.4-0.8 mm). The cannula 14 of the first preferred embodiment may be a cannula gage 27 and the cannula gap distance X between the first skin contacting surface 34 and an outer diameter of the cannula 14 may be fifty-five hundredths of a millimeter (0.55 mm) or greater, generally resulting in the tip 14a of the cannula 14 being positioned within the dermal layer in the injection position. The cannula gap distance X may be impacted by the orientation of the cannula 14 (lancet up or lancet down), gage of the cannula 14, expected location of injection in the patient and numerous other factors that may be considered by the designer.

In the first preferred embodiment, the tip 14a of the cannula 14 is positioned approximately one and one-half to ten millimeters (1.5-10 mm) along the longitudinal axis 18 from the demarcation plane 27 defined where the cannula 14 extends over the channel edge 26a. The demarcation plane 27 intersects and is generally perpendicular to the longitudinal axis 18. In the first preferred embodiment, the tip 14a of the cannula 14 is positioned distally beyond the demarcation plane 27, defined where the cannula 14 extends over the channel edge 26a, at an exposed length $L_1$. The exposed length $L_1$ is not limited to the above-described one and one-half to ten millimeters (1.5-10 mm) and may have nearly any length that permits insertion of the tip 14a into the dermal layer of the patient's skin S in the injection configuration. In a more preferred range, the exposed length $L_1$ is approximately two and one-half to seven millimeters (2.5-7 mm) and in a further preferred range, the exposed length $L_1$ is approximately two and one-half to four millimeters (2.5-4 mm). In the assembled configuration, the exposed length $L_1$ is preferably predetermined during the design of the adapter 10 and the cannula 14 generally does not move or slide relative to the adapter in the assembled configuration. Accordingly, once the syringe 12 is engaged with the adapter 10 of the first preferred embodiment, the exposed length $L_1$ generally does not change and the cannula 14 and associated syringe 12 do not slide relative to the body 16, the central portion 24 and the distal protrusion 30.

The distal protrusion 30 of the first preferred embodiment is generally clear or transparent, at least distally toward the distal nose 32 relative to the demarcation plane 27, and is generally cloudy or opaque proximally of the demarcation plane 27. The central portion 24 and the remainder of the adapter 10 are also preferably cloudy or opaque. Providing a generally transparent distal protrusion 30, at least distally of the demarcation plane 27, and a generally opaque distal protrusion 30 and adapter 10 proximally of the demarcation plane 27 provides a visual cue to a medical professional or user that the cannula 14 is penetrating the skin S during injection and that the skin S is in facing engagement with the first skin contacting surface 34 in the injection position. The distal portion of the cannula 14 may appear to disappear or be completely positioned beneath the skin S in the injection position due to the generally transparent distal protrusion 30 distally relative to the demarcation plane 27 and cloudy or opaque remainder of the adapter 10, as the proximal portion of the cannula 14 that is positioned proximally to the demarcation plane 27 may be obscured by the opaque or cloudy portions of the adapter 10. This disappearance of the cannula 14 also provides a visual cue to the medical professional or user that the cannula 14 penetrates the skin S a sufficient distance and additional insertion pressure or force is not required to insert the cannula 14. This visual cue can be particularly useful for "heavy-handed" medical professionals or users who may apply excessive pressure in the injection position and potentially cause skin S to bunch between the first skin contacting surface 34 and the cannula 14, which could cause damage to the cannula 14 or result in the tip 14a being positioned outside of the intradermal layer.

Designing the distal protrusion 30 with a generally transparent portion distally and a generally opaque portion proximally of the demarcation plane 27 permits the medical professional or user to visually confirm that the distal portion of the cannula 14 that extends beyond the cannula channel edge 26a has entered the patient's skin S and the skin S is in relatively consistent contact with the first skin contacting surface 34, which provides a visual indication to the medical professional or user that the tip 14a of the cannula 14 is positioned in the dermis or dermal layer of the patient's skin S such that the medicament will be injected into the dermis or dermal layer of the patient's skin S for absorption into the patient's body.

In the first preferred embodiment, a tip 14a of the cannula 14 is preferably spaced at an overhang length $L_2$ from a distal edge of the distal nose 32. The overhang length L2 is preferably at least one millimeter (1 mm), particularly if the adapter 10 does not include the upturned distal nose 32. In the first preferred embodiment, the overhang length $L_2$ is approximately two to six millimeters (2-6 mm). The overhang length $L_2$ provides some safety to users and patients from receiving an inadvertent puncture from exposure to the tip 14a, for example, if a medical professional attempts to introduce the cannula into the skin S generally perpendicular to the skin S or inadvertently approaches the skin S generally perpendicularly to the skin S, and also provides a section of relatively constant cannula gap distance X between the tip 14a and the demarcation plane 27 in the assembled configuration to correctly position the tip 14a in the skin S during insertion. The cannula gap distance X is preferably consistent between the demarcation plane 27 and the tip 14 as a result of at least the distal portion of the cannula 14 extending generally parallel to the first skin contacting surface 34. The first skin contacting surface 34 also preferably extends beyond the tip 14a along a generally linear or parallel path, at least for a limited distance before the distal nose 32 begins to curve upwardly and this extended distance may be approximately one to two millimeters (1-2 mm). The overhang length $L_2$ is not limited to the above-described dimensions and may have nearly any dimension that limits exposure to the tip 14a and facilitates insertion of the cannula 14 into the skin S at a desired depth from the surface of the skin S. The overhand length $L_2$ also generally prevents perpendicular insertion of the cannula tip 14a into the patient's skin S. Attempts at perpendicular insertion of the cannula tip 14a into the patient's skin S typically produces inaccurate positioning of the tip 14a in the dermal layer and injection of the medicament into an undesirable section of the skin S.

Referring to FIGS. 1 and 2 in the first preferred embodiment, the syringe 12 includes a barrel 44, a plunger 46 with a piston 46a slidable and sealingly engaged within a hollow cavity 44a of the barrel 44 and the cannula 14. The barrel 44a has a generally cylindrical configuration and the hollow internal cavity 44a receives the medicament therein. The medicament is typically stored between the piston 46a and the cannula 14 in the hollow internal cavity 44a. The syringe 12 is not limited to inclusion of the barrel 44, plunger 46 and cannula 14 and may be comprised of nearly any device that is able to retain medicament therein, be joined with the adapter 10 and expel the medicament therefrom or otherwise inject the medicament into the dermal layer of the patient's skin S in operation. For example, the syringe 12 may be comprised of a pre-filled syringe 12 without a cannula 14 wherein the cannula 14 is associated with the adapter 10 (See e.g. FIGS. 11 and 12).

In the first preferred embodiment, the adapter 10 includes at least the body 16, the distal nose 32, the central portion 24 and the syringe channel 20 that extends generally parallel to the longitudinal axis 18 through the body 16. The body 16 includes the syringe channel 20 and is preferably positioned proximally on the adapter 10 relative to the central portion 24, which includes the cannula channel 26. The syringe channel 20 receives at least a portion of the syringe 12 and, particularly, at least a portion of the barrel 44 in the assembled configuration. The adapter 10 also includes the side opening 22 that preferably extends along an entire length of the adapter 10 between the proximal portion 16a and the distal nose 32 or at least to the end of the central portion 24 near the cannula channel edge 26a. The side opening 22 permits selective insertion of the syringe 12 and cannula 14 relative to or into the adapter 10. The side opening 22 is preferably slightly narrowed relative to a maximum diameter of the barrel 44 such that the barrel 44 is force-fit or snap-fit into the syringe channel 20 during assembly. The snap-fit or force-fit of the barrel 44 into the syringe channel 20 assist in retaining the syringe 12 in the adapter 10 following assembly. However, the barrel 44 is not limited to being snap-fit or force-fit into the syringe channel 20 and may be alternatively engaged or secured to the adapter 10 by staking, clamping, adhesive bonding, fastening or otherwise fastening or securing the syringe 12 to the adapter 10.

In the first preferred embodiment, the configuration of the syringe channel 20 inside opening 22 defines a narrowed C-shaped clamping section into which the syringe 12 is force fit in the assembled configuration.

Figure 5:
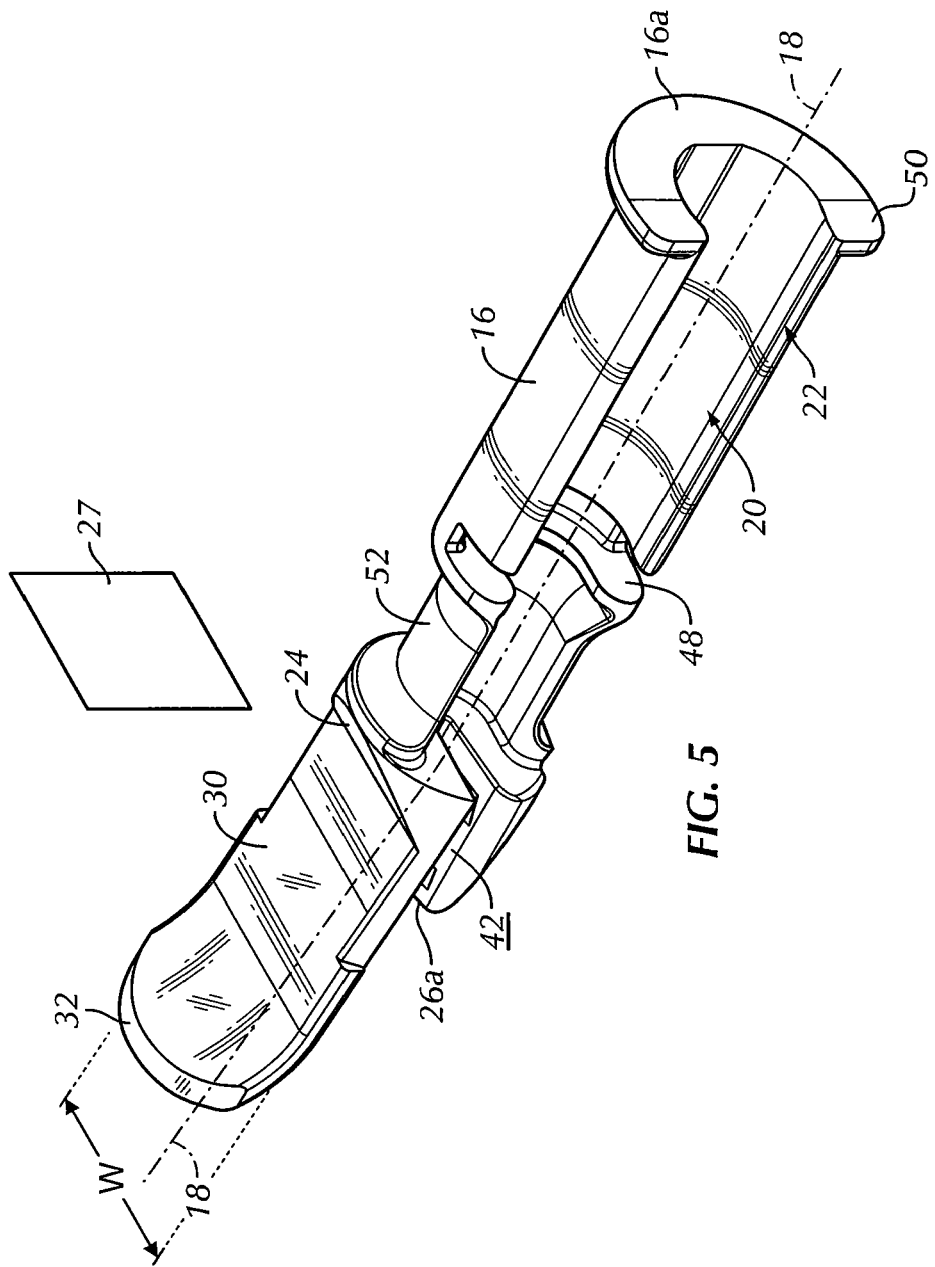
FIG. 5 is a rear perspective view of the adapter of FIG. 1.
Figure 8:
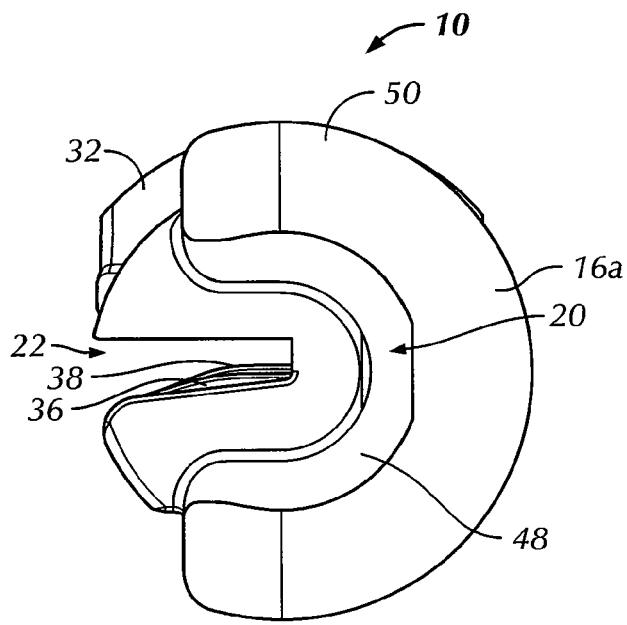
FIG. 8 is a rear elevational view of the adapter of FIG. 1.
Figure 10:
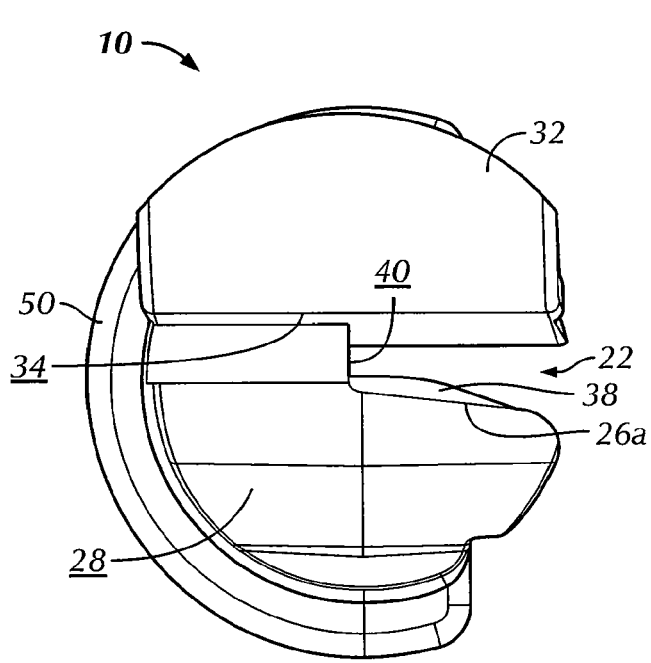
FIG. 10 is a front elevational view of the adapter of FIG. 1.
Figure 9:
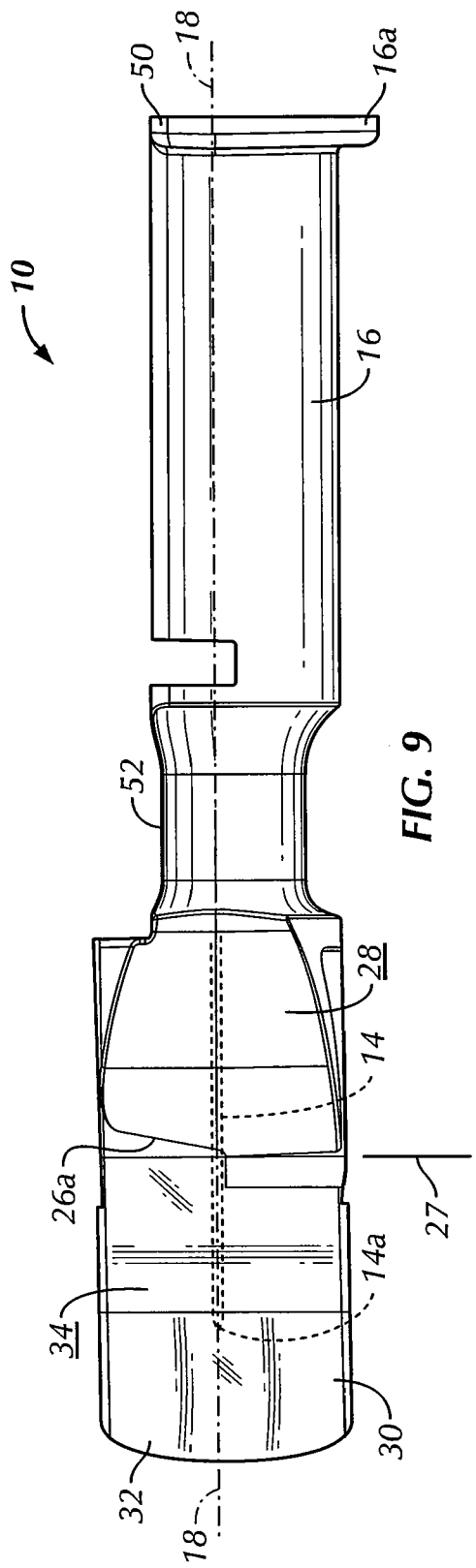
FIG. 9 is a bottom plan view of the adapter of FIG. 1.

Referring to FIG. 5, the distal protrusion 30 has a protrusion width W of approximately three to ten millimeters (3-10 mm) to engage the skin S in the injection position (FIG. 2). The protrusion width W is not limited to the three to ten millimeter (3-10 mm) range and may have nearly any width that is maneuverable by the medical professional or user and promotes proper placement of the tip 14a in the dermal layer or dermis in the injection position. In the first preferred embodiment, the protrusion width W is approximately the same or slightly smaller than the diameter of the barrel 44, but is not so limited. It may be preferable for the protrusion width W to generally match or be slightly smaller than the diameter of the barrel 44 for storage, packaging, maneuverability and overall handling of the syringe 12 and adapter 10. The protrusion width W is preferably configured to result in minimization of forces required during insertion while generally stabilizing the position of the adapter 10 relative to the skin S during insertion and in the injection position. The protrusion width W of the distal protrusion 30 could be narrow relative to the barrel 44 to integrate other system components or may be larger than the barrel 44 of the syringe 12 to generally maximize stability.

Referring to FIGS. 1-3, in the first preferred embodiment, the cannula 14 has a cannula hub 14b that is preferably, integrally engaged with a narrowed distal portion 44b of the syringe 12. The cannula 14 is preferably constructed of a metal material that is bonded into the cannula hub 14b, which is typically constructed of a polymeric or plastic material. The adapter 10 also preferably includes a positioning wall 48 that is engaged with the narrowed distal portion 44b of the barrel 44 in the assembled configuration. Engagement of the narrowed distal portion 44b and the positioning wall 48 generally controls the positioning of the tip 14a of the cannula 14 relatively along the longitudinal axis 18 to obtain the desired exposed length $L_1$ and overhang length $L_2$ Accordingly, the adapter 10 is preferably configured for syringes 12 and cannulas 14 having known dimensions, at least with respect to the position of the narrowed distal portion 44b relative to the tip 14a of the cannula 14 such that the positioning of the tip 14a relative to the adapter 10 is controllable. The syringe channel 20 is also designed and configured to receive and retain the barrel 44 of the syringe 12 in the assembled configuration.

In the first preferred embodiment, the adapter 10 includes a collar 50 at the proximal end portion 16a that can be utilized by a user to handle the adapter 10. The collar 50 may be used to engage the adapter 10 with the user's fingers to maintain the syringe 12 in a proper position relative to the adapter 10.

The adapter 10 also preferably includes a finger grasping portion 52 that can be utilized by the medical professional or nurse to grasp and hold the adapter 10 and syringe 12 during use. The finger grasping portion 52 permits the medical professional or nurse to grasp the adapter 10 and syringe 12 proximate the distal nose 32 to provide control close to the tip 14a. During injection, the medical professional typically manipulates the assembled adapter 10 and syringe 12 by grasping the barrel 44 and/or the adapter 10.

Referring to FIGS. 11 and 12, in a second preferred embodiment, an adapter 10' has a similar configuration to the adapter 10 of the first preferred embodiment, but the cannula 14' is fixed to the adapter 10', the body 16' does not include a side opening for receipt of the syringe 12', as well as additional structural and functional differences between the first and second embodiment. The adapter 10' of the second preferred embodiment utilizes the same reference numerals to identify similar features relative to the adapter 10 of the first preferred embodiment and a prime symbol (') to specifically identify the adapter 10' of the second preferred embodiment and its components. Accordingly, a significant number of the features of the second preferred embodiment of the adapter 10' are the same or similar to the adapter 10 of the first preferred embodiment and the features that are different in the adapter 10' of the second preferred embodiment are emphasized in the below description.

In the second preferred embodiment, the cannula 14' is fixed to the adapter 10' such that the tip 14a' is positioned relative to the distal protrusion 30' with the exposed length $L_1$ and the overhang length $L_2$ predetermined and typically falling within the above-described predetermined ranges of the first preferred embodiment. In addition, the cannula gap distance X' is also predetermined and preferably falls within the above-described preferred ranges of the first preferred embodiment. Fixing the cannula 14' to the adapter 10' generally eliminates potential mis-alignment of the cannula 14' relative to the adapter 10 and, therefore, mis-positioning of the tip 14a' relative to the distal protrusion 30'.

In the second preferred embodiment, the adapter 10' is typically associated with a pre-filled syringe (not shown) without the cannula 14' mounted thereto and is typically attached to the proximal end portion 16a' of the body 16' using a conventional Luer. The syringe 12' may be pre-filled by the manufacturer, filled by the medical professional or user prior to injection or otherwise filled prior to engaging the adapter 10' with the pre-filled syringe 12' using a cannula, vial adapter, spike or other mechanism. The syringe 12' is not limited to being mounted to the body 16' by a Luer in the second preferred embodiment and may be otherwise mounted, secured or fastened to the body 16'.

Figure 15:
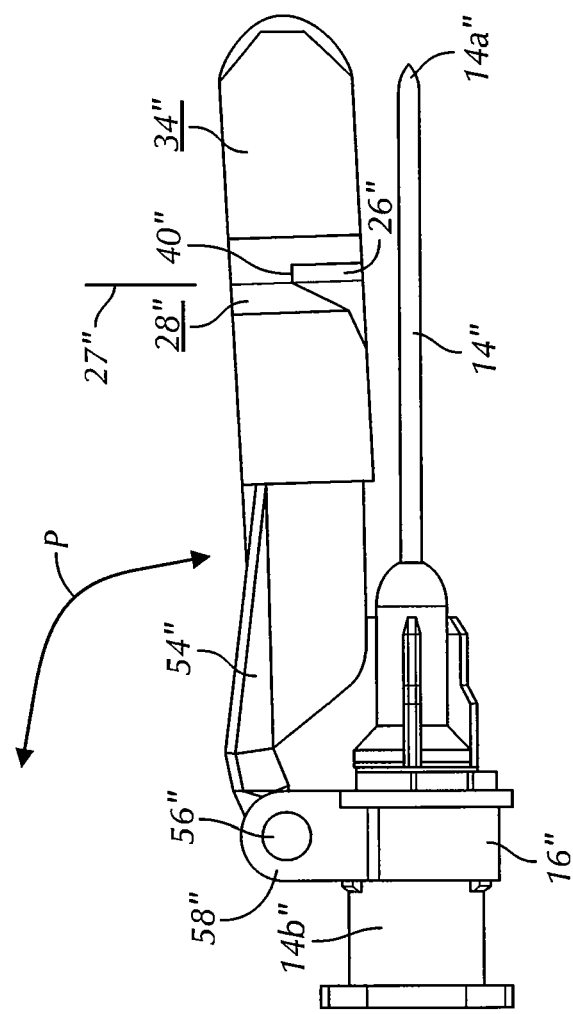
FIG. 15 is a magnified bottom plan view of the adapter of FIG. 13 mounted to the distal end portion of a syringe.

Referring to FIGS. 13-15, in a third preferred embodiment, an adapter 10" has a similar configuration to the adapters 10, 10' of the first and second preferred embodiments, but the body 16" is pivotable relative to the central portion 24" and the distal protrusion 30" such that the central portion 24" and the distal protrusion 30" may be pivoted away from the cannula 14" in an aspiration position and pivoted into proximity or engagement with the cannula 14" in an assembled configuration. In the third preferred embodiment, the central portion 24" and the distal protrusion 30" are pivotable relative to the body 16" along a generally arcuate path indicated by a pivoting arrow P. Additional differences between the third preferred embodiment of the adapter 10" and the other embodiments are described below or can generally be identified in the figures. The distal protrusion 30" and central portion 24"

are not limited to being pivotable relative to the cannula 14" and body 16" and may slide relative to the cannula 14" and body 16" or otherwise move or reposition relative to the cannula 14" and body 16" to alternatively expose the cannula 14" and move or reposition into the assembled configuration. The adapter 10" of the third preferred embodiment utilizes the same reference numerals to identify similar features relative to the adapters 10, 10' of the first and second preferred embodiments and a double-prime symbol (") to specifically identify the adapter 10" and its components of the third preferred embodiment. Accordingly, a significant number of the features of the third preferred embodiment of the adapter 10" are the same or similar to the adapters 10, 10' of the first and second preferred embodiments and the features that are different in the third preferred embodiment of the adapter 10" are emphasized in the below description.

The body 16" of the adapter 10" of the third preferred embodiment has a generally ring-like shape with the syringe channel 20" extending therethrough. The body 16" is configured to engage the cannula hub 14b", the narrowed distal portion 44b", a distal portion of the hub 44" and/or another portion of the syringe 12" to secure the adapter 10" to the syringe 12". The body 16" is pivotably secured to the central portion 24" and the distal protrusion 30" by a pivot arm 54", a pivot shaft 56" and a pivot hub 58". In the third preferred embodiment, the pivot hub 58" is formed as a portion of the body 16" and the pivot arm 54" and pivot shaft 56" are formed as a portion of the central portion 24" and the distal protrusion 30", such that the central portion 24" and the distal protrusion 30" are able to pivot relative to the body 16" and the syringe 12" in an assembled configuration when the body 16" is mounted to the syringe 12". Alternatively, the body 16" may be formed as a single molding with the pivot arm 54" and the distal protrusion 30" and may include a living hinge (not shown) positioned between the body 16" and the pivot arm 54" to permit pivoting between the body 16" and the central portion 24" and the distal protrusion 30". Similar to the first and second preferred embodiments, the distal protrusion 30" of the adapter 10" is preferably clear or at least partially transparent distally relative to the demarcation plane 27" such that the medical professional can visually monitor the cannula 14" and/or the skin S during assembly and use. The body 16" is also configured to selectively receive a cap (not shown) such that the cannula 14" can be covered when the distal protrusion 30" and pivot arm 54" are pivoted away from the cannula 14".

The adapter 10" of the third preferred embodiment is configured for side insertion of the cannula 14" into the cannula channel 26", which has a generally V-shape with a wide portion at a side proximate the pivot arm 54" and a narrow apex that forms the lateral cannula wall 40" opposite the wide portion. The V-shaped cannula channel 26" guides the cannula 14" into a proper position relative to the distal protrusion 30", similar to the first and second alignment ramps 36, 38 and the lateral cannula wall 40" of the adapter 10 of the first preferred embodiment.

In the third preferred embodiment, the pivot shafts 56" preferably have an interference fit with the pivot hub 58". The ring-shaped body 16" is preferably urged onto the barrel 44" or the hub 14b" during assembly and retains the adapter 10" relative to the syringe 12" in the assembled configuration. The body 16" may engage the syringe 12" by force-fit surface contact, tongue and groove engagement, protrusions, bayonet-type engagement, clamping, fastening, adhesive bonding or nearly any mechanism or method that permits engagement of the body 16" with the syringe 12" such that the distal protrusion 30" may be pivoted into the injection position relative to the cannula 14". The cannula 14" is captured and aligned by the V-groove of the cannula channel 26" of the central portion 24" such that the cannula 14" is preferably positioned near the narrow apex of the lateral cannula wall 40" of the third preferred embodiment. A distal section of the cannula 14" and the cannula tip 14a" protrude through the cannula channel 26" below the first skin contacting surface 34". The distal protrusion 30" and the pivot arm 54" may be locked in the injection position relative to the cannula 14" after the distal protrusion 30" and the pivot arm 54" are pivoted into the injection position following aspiration of the medicament, but is not limited to being locked or otherwise secured in the injection position.

The V-groove of the cannula channel 26" may also be arranged such that the wide-portion of the V-groove cannula channel 26" is positioned opposite or faces away from the distal protrusion 30". In such a configuration, the wide-portion or mouth of the V-groove cannula channel 26" extends through the second skin contacting surface 28" such that the first skin contacting surface 34" is urged along an arc onto or away from a top of the cannula 14" when the central portion 24" and distal protrusion 30" are pivoted to and from the injection position. That is, in this alternative arrangement of the adapter 10" of the third preferred embodiment, the wide portion of the V-groove shaped cannula channel 26" is positioned generally along a surface of the central portion 24 opposite the distal protrusion 30" or on a bottom surface of the adapter 10". In contrast, in the third preferred embodiment, the wide-portion or mouth of the V-groove cannula channel 26" is located in a side of the central portion 24".

Referring to FIGS. 16 and 17, in a fourth preferred embodiment, an adapter 10''' has a similar configuration to the adapters 10, 10', 10" of the first, second and third preferred embodiments, but the adapter 10' is formed integrally with or is fixedly secured to the syringe 12'''. The adapter 10''' of the fourth preferred embodiment utilizes the same reference numerals to identify similar features relative to the adapters 10, 10', 10" of the first, second and third preferred embodiments and a triple-prime symbol (''') to specifically identify the adapter 10''' and its components of the fourth preferred embodiment. Accordingly, a significant number of the features of the fourth preferred embodiment of the adapter 10''' are the same or similar to the adapters 10, 10', 10" of the first, second and third preferred embodiments and the features that are different in the fourth preferred embodiment of the adapter 10''' are emphasized in the description below.

The adapter 10''' of the fourth preferred embodiment is generally intended for a pre-filled arrangement, wherein the syringe 12''' is permanently fixed to or integrally formed with the adapter 10''' and packaged in a sterile package for transportation and/or storage. The adapter 10''' preferably has a diameter at the central portion 24''' that is approximately the same as the diameter of the barrel 44''' of the syringe 12''', but is not so limited. In addition, the body 16''' of the adapter 10''' of the fourth preferred embodiment is permanently bonded or integrally formed with the barrel 44''' of the syringe 12'''. The diameter of the central portion 24''' and/or the body 16''' may be smaller or larger than the diameter of the barrel 44''' or may be otherwise shaped as an oval, square, rectangle or other shape that is formed with or permanently engaged with the barrel of the syringe 12'''. For example, the adapter 10''' of the fourth preferred embodiment may be comprise of an integrally molded polymeric material that is formed at the same time as the barrel 44''', may be assembled to the barrel 44''' of the syringe 12''', which may be constructed of a glass material, or may be otherwise permanently secured to the syringe 12''' during manufacturing of the syringe 12'''.

The adapter 10''' and syringe 12''' that are either integrally formed or assembled during the manufacturing process permits the manufacturer to define alignment of the cannula 14''' with the first skin contacting surface 34''', the cannula gap distance X''', the entire fluid flow path between the barrel 44''' and the tip 14a''' (preferably limiting or shortening this flow path) and the position and orientation of the cannula 14''' relative to the longitudinal axis 18'''. The integrally formed or assembled adapter 10''' of the fourth preferred embodiment also permits the manufacturer to maintain sterility of the cannula 14''' and the adapter 10''' section contacting the skin from the time the adapter 10''' and syringe 12''' are initially packaged until the adapter 10''' and syringe 12''' are removed from the packaging, which preferably occurs immediately before the injection process. The adapter 10''' of the fourth preferred embodiment further permits the manufacturer to seal the fluid path from the barrel 44''' to the tip 14a''' such that medicament does not leak from the flow path due to faulty components to mistakes during assembly in the field by the user. The manufacturer is also able to predetermine the orientation of the tip 14a''' of the cannula 14''' in a lancet up orientation, a lancet down orientation or in nearly any orientation that is deemed advantageous by the manufacturer or preferred by the user.

In the fourth preferred embodiment, the adapter 10''' also preferably includes an elastomeric cap 60''' that is removably mountable over the adapter 10''' and onto the barrel 44''' of the syringe 12''' or onto the hub 14b''' to generally protect the adapter 10''' during transportation and storage, seal the tip 14a''' of the cannula 14''' to maintain the medicament in the barrel 44''' and to generally maintain the sterility of the adapter 10''' until the medical professional or other user is prepared to give the injection to the patient. The elastomeric cap 60''' is preferably constructed of an elastomeric material that is able to conform to, engage and seal to the barrel 44''' and other portions of the adapter 10''' to seal the medicament in the barrel 44''' and generally maintain sterility of the adapter 10''' when the cap 60''' is secured to the syringe 12'''. The cap 60''' is preferably force-fit onto the syringe 12''' in an assembled configuration (not shown) such that the tip 14a''' is positioned within the material of the elastomeric cap 60''' to block a flow path out of the tip 14a''' and generally maintain the medicament in the barrel 44''' or generally prevent medicament leakage when the cap 60''' is secured to the adapter 10'''.

The diameter of the cap 60''' may exceed that of the barrel 44''', may be relatively the same or may be slightly smaller, depending upon manufacturing equipment and/or user and design preferences. The cap 60''' is preferably mounted on the syringe 12''' and adapter 10''' by pushing the cap 60''' onto and toward the barrel 44''' such that the cap 60''' engages and is compressed around a distal end portion of the barrel 44''' and the tip 14a''' is positioned within elastomeric material at a distal head portion 60a''' of the cap 60'''. The preferred force-fit of the cap 60''' onto the barrel 44''' and embedding of the tip 14a''' into the material of the distal head portion 60a''' generally improves sterility or maintenance of sterility of the adapter 10''' until the cap 60' is removed from the adapter 10''' prior to injection of the medicament into the patient. The tip 14a''' is generally maintained in the distal head portion 60a''' in a storage position until immediately prior to injection of the medicament into the patient to reduce the likelihood that the adapter 10''' and/or cannula 14''' become contaminated and that medicament leaks from the syringe 12'''. The cap 60''' is not limited to being comprised of a single elastomeric component and may be comprised of multiple components that are elastomeric or a combination of elastomeric and relatively rigid materials that generally cover and protect the adapter 10''' during storage, transport and prior to the injection process. For example, the cap 60''' may be comprised of an elastomeric material positioned within a generally rigid polymeric shell that functions in a similar manner to the above-described elastomeric cap 60'''.

Referring to FIGS. 1-10, in operation, the syringe 12 is either provided pre-filled or the medicament is aspirated into the syringe 12 from a vial (not shown). The syringe 12 may be separate from the adapter 10 to aspirate the medicament into the syringe 12 and a different cannula 14 may be utilized to aspirate the medicament into the syringe 12 than is used to inject the medicament into the patient. For example, a relatively large gage cannula 14 may be used to aspirate the medicament into the barrel 44 and the relatively large gage cannula 14 may be replaced with a smaller gage cannula 14 for injection. Alternatively, the central portion 24 and distal protrusion 30 may be hingedly mounted to the barrel 44 and/or hub 14b and the cannula 14 such that the central portion 24 and distal protrusion 30 may be pivoted away from the cannula 14 during aspiration of medicament from the vial into the syringe 12 and then pivoted back into the assembled configuration for the injection procedure.

After medicament is in the syringe 12, the syringe 12 is mounted to the adapter 10. Preferably, the syringe 12 is press-fit through the side opening 22 into the syringe channel 20 to engage the syringe 12 with the adapter 10. In the assembled configuration, the narrow distal portion 44b is preferably positioned in facing engagement with the positioning wall 48 to properly locate the tip 14a relative to the adapter 10. Once the narrow distal portion 44b is positioned in facing engagement with the positioning wall 48, the cannula 14 generally does not move relative to the adapter 10.

In the preferred assembled configuration, at least a portion of the cannula 14 is positioned within the cannula channel 26. During insertion from the side, the cannula 14 is guided into the cannula channel 26 by moving along the upslope surfaces 36a, 38a of the first and second alignment ramps 36, 38, over the apex-surfaces 36b, 38b and along the downslope surfaces 36c, 38c. In the assembled configuration, the cannula 14 is preferably positioned in facing engagement with the downslope surfaces 36c, 38c and the lateral cannula wall 40. Positioning of the needle 14 in this configuration urges the cannula 14 into generally parallel alignment with the first skin contacting surface 34 such that the cannula 14 is spaced from the first skin contacting surface 34 by the cannula gap distance X. The cannula gap distance X is preferably predetermined such that the tip 14a is positioned in the dermal layer of the patient's skin S in the injection position.

To inject the medicament into the patient's skin S, the user may grasp the finger grasping portion 52 and/or the barrel 44 and urge the adapter 10 into engagement with the patient's skin S. The adapter 10 is oriented relative to the patient's skin S such that the longitudinal axis 18 is slightly less than parallel or nearly parallel relative to the user's skin S. Referring specifically to FIG. 2A, the adapter 10 may be urged slightly downwardly toward the skin S and is subsequently urged toward or slides along the user's skin S such that at least the first skin contacting surface 34 is in engagement with a surface of the epidermis of the skin S. As the adapter 10 slides along the skin S, the distal nose 32 promotes relatively smooth sliding of the adapter 10 along the skin S. The cannula 14 generally does not move relative to the adapter 10 during the injection process and the cannula 14 preferably enters the skin S for approximately the entire exposed length $L_1$. The medical professional or user is able to visually inspect the cannula 14 entering the skin S and the surface of the epidermis contacting the first skin contacting surface 34 through the transparent distal portion of the distal protrusion 30, which is demarcated by the preferred transparent to opaque transition of the distal protrusion 30 at the demarcation plane 27. In a fully engaged injection position, the user or medical professional may visually observe that the entire portion of the cannula 14 positioned distally of the demarcation plane 27 is positioned within the skin S. Accordingly, the medical professional may note that the cannula 14 is not visible through the relatively transparent portion of the distal protrusion 30 because the cannula 14 is located within the skin S. During insertion and injection, the medical professional or nurse is also able to view the tip 14a entering the skin S through the generally transparent distal protrusion 30. In addition, the nurse or medical professional is generally able to see the skin S contacting the first skin contacting surface 34 through the distal protrusion 30. Further, the first and second skin contacting surfaces 34, 28 promote positioning of the cannula 14 relative to the skin S to further promote positioning of the tip 14a of the cannula 14 into the dermal layer. In the injection position, the tip 14a of the cannula 14 is positioned in the dermis of the skin S.

Once the tip 14a of the cannula 14 is properly positioned in the skin S, the plunger 46 is depressed, thereby urging the piston 46a to push the medicament out of the barrel 44, through the cannula 14, out of the tip 14a and into the dermal layer. The medicament is absorbed into the dermal layer to provide clinical benefits to the patient.

The cannula gap distance X is designed to position the tip 14a of the cannula 14 in the dermal layer in the injection position (FIG. 2). Although the epidermis and dermal layers of the skin S can have variable thicknesses, the cannula gap distance X is designed to result in the tip 14a being positioned in the dermis or at the lower portion of the epidermis in the injection position for the most common thicknesses of the epidermis and dermis of typical skin S. Accordingly, the combination of the adapter 10 and the syringe 12 provide a relatively high likelihood that the tip 14a is positioned in the dermis or dermal layer and provides clinical benefit for the patient by applying the medicament directly to the preferred layer of the skin S. Following injection, the syringe 12 and adapter 10 are withdrawn away from the skin S, typically in an opposite direction from insertion and the syringe 12 and adapter 10 are discarded.

Referring to FIGS. 1, 11 and 12, in operation of the second preferred embodiment of the adapter 10', the injection and process is typically the same with the exception that the pre-filled syringe 12 without the cannula 14 is mounted to the proximal end portion 16a' of the body 16' and the cannula 14' is fixed to the adapter 10'.

Referring to FIGS. 13-15, the adapter 10" of the third preferred embodiment is mounted to the syringe 12" by securing the body 16" to the barrel 44" and/or hub 14'", as was described above. The syringe 12" may be pre-filled or the pivot arm 54" and distal protrusion 30" may be pivoted away from the cannula 14" such that the medicament may be aspirated into the barrel 44", as would be apparent to one having ordinary skill in the art. The pivot arm 54", the central portion 24" and the distal protrusion 30" are then pivoted toward the cannula 14" until the distal portion of the cannula 14" is properly positioned relative to the first skin contacting surface 34", preferably co-axially with the longitudinal axis 18". In the injection position, a portion of the cannula 14" is preferably positioned in proximate the apex of the cannula channel 26" at the lateral cannula wall 40". The medicament may then be injected into the patient utilizing the above-described technique, which was described in detail with respect to the adapter 10 of the first preferred embodiment.

Referring to FIGS. 2, 16 and 17, utilizing the adapter 10'" and syringe 12'" of the fourth preferred embodiment typically results in the medical professional initially removing the adapter 10'" and syringe 12'" from a sterile packaging shortly before the injection process. The patient is prepared for the injection and the cap 60'" is moved away from the barrel 44'" to release the cap 60'" from the syringe 12'". The sterility of the adapter 10'" is generally maintained and the fluid path is generally closed, at least until the cap 60'" is removed from the barrel 44'", as the cannula 14'" and adapter 10'" are constantly protected by the cap 60'". The syringe 12'" and adapter 10'" are aligned with the patient's skin S such that the longitudinal axis 18'" is generally parallel to or slightly pitched relative to the surface of the skin S, the first skin contacting surface 34'" engages the surface of the skin S to align the syringe 12'" and adapter 10'" with the skin S and the syringe 12'" and adapter 10'" are urged distally such that the cannula 14'" penetrates the skin S. The tip 14a'" preferably enters the skin S and is guided into the dermal layer or dermis by the configuration of the adapter 10'". The medical professional or other user verifies that the cannula 14'" has is entering the skin S and the surface of the skin S is positioned in engagement with the first skin contacting surface 34'" by visually confirming the position of the cannula 14'" and the skin S through the generally transparent distal protrusion 30'" during injection. The cannula 14'" may visually disappear from the medical professional and/or user's view in the in the injection position. When the medical professional or other user verifies the penetration of the cannula 14'" into the skin S and the positioning of the skin S relative to the first skin contacting surface 34'", the medicament is injected into the dermal layer or dermis by depressing the plunger 46'" toward the cannula 14'", thereby urging the medicament out of the tip 14a'" and into the patient. The syringe 12'" and adapter 10'" are subsequently moved away from the patient's skin S, generally parallel to the surface of the patient's skin S and discarded.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An intradermal injection assembly for injecting a medicament into a dermal skin layer, the assembly comprising:
   a syringe including a cannula (14) with a tip (14a), a hub (14b), a barrel (44) and a plunger (46), the barrel having a generally cylindrical configuration and a hollow internal cavity adapted to receive the medicament therein; and
   an adapter (10) having a body (16) with a syringe channel (20), a central portion (24) with a cannula channel defining a cannula channel edge (26a), an alignment ramp (36) positioned within the cannula channel, and a distal protrusion with a distal nose (32), a generally continuous first skin contacting surface, a proximal end portion and a longitudinal axis (18) extending between the proximal end portion and the distal nose, wherein the generally continuous first skin contacting surface (34) is positioned generally parallel to the longitudinal axis, a distal portion of the cannula being spaced from the first skin contacting surface at a cannula gap distance (X) in the assembled configuration, the tip (14a) of the cannula being positioned distally relative to the cannula channel edge in an assembled configuration, wherein an opening (22) extends along an entire length of the adapter generally parallel to the longitudinal axis for selective insertion and removal of the barrel generally transverse to the longitudinal axis and the alignment ramp orients a distal portion of the cannula generally parallel with the first skin contacting surface in the assembled configuration to control spacing of the cannula relative to the first skin contacting surface such that the tip of the cannula is configured for positioning in the dermal skin layer when the intradermal injection assembly is in an injection position.

2. The assembly of claim 1 wherein the tip of the cannula is located approximately one to six millimeters (1-6 mm) from the distal nose in the assembled configuration.

3. The assembly of claim 1 wherein the distal protrusion is generally transparent distally relative to a demarcation plane (27) defined where the cannula crosses the cannula channel edge in the assembled configuration, the distal protrusion and central portion of the adapter being generally opaque proximally relative to the demarcation plane.

4. The assembly of claim 1 wherein the distal nose curves away from the longitudinal axis.

5. The assembly of claim 1 wherein the cannula is positioned at least partially within the cannula channel in the assembled configuration.

6. The assembly of claim 1 further comprising:
an elastomeric cap (60") removably mountable over the adapter and a portion of the barrel such that the tip of the cannula is positioned within a distal head portion (60a") of the elastomeric cap in a storage position.

7. The assembly of claim 1 wherein the tip of the cannula is spaced an exposed length from a demarcation plane defined by the cannula channel edge.

8. The assembly of claim 7 wherein the exposed length is approximately one and one-half millimeters to ten millimeters (1.5-10 mm).

* * * * *